United States Patent
Takahashi et al.

(10) Patent No.: US 9,012,493 B2
(45) Date of Patent: *Apr. 21, 2015

(54) 1-HETERODIENE DERIVATIVE AND PEST CONTROL AGENT

(75) Inventors: Jyun Takahashi, Odawara (JP); Takehiko Nakamura, Odawara (JP); Masahiro Miyazawa, Odawara (JP); Isami Hamamoto, Odawara (JP); Jyun Kanazawa, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 265 days.

This patent is subject to a terminal disclaimer.

(21) Appl. No.: 13/261,290

(22) PCT Filed: Nov. 9, 2010

(86) PCT No.: PCT/JP2010/069915
§ 371 (c)(1),
(2), (4) Date: May 9, 2012

(87) PCT Pub. No.: WO2011/058963
PCT Pub. Date: May 19, 2011

(65) Prior Publication Data
US 2012/0225895 A1    Sep. 6, 2012

(30) Foreign Application Priority Data

Nov. 12, 2009 (JP) ................. 2009-258651

(51) Int. Cl.
| | | |
|---|---|---|
| A01N 43/10 | (2006.01) | |
| A01N 43/18 | (2006.01) | |
| C07D 333/36 | (2006.01) | |
| A01N 43/12 | (2006.01) | |
| A01N 43/16 | (2006.01) | |
| A01N 43/40 | (2006.01) | |
| A01N 43/54 | (2006.01) | |
| A01N 43/60 | (2006.01) | |
| A01N 43/713 | (2006.01) | |
| A01N 43/78 | (2006.01) | |
| C07D 335/02 | (2006.01) | |
| C07D 409/12 | (2006.01) | |
| C07D 417/12 | (2006.01) | |

(52) U.S. Cl.
CPC ............. *C07D 333/36* (2013.01); *A01N 43/10* (2013.01); *A01N 43/12* (2013.01); *A01N 43/16* (2013.01); *A01N 43/18* (2013.01); *A01N 43/40* (2013.01); *A01N 43/54* (2013.01); *A01N 43/60* (2013.01); *A01N 43/713* (2013.01); *A01N 43/78* (2013.01); *C07D 335/02* (2013.01); *C07D 409/12* (2013.01); *C07D 417/12* (2013.01)

(58) Field of Classification Search
CPC ..... A01N 43/10; A01N 43/18; C07D 333/36; C07D 335/02

USPC ............... 549/28, 68; 514/432, 438, 447
See application file for complete search history.

(56) References Cited

U.S. PATENT DOCUMENTS

| | | | |
|---|---|---|---|
| 4,476,307 A | 10/1984 | Howard, Jr. et al. | |
| 4,950,666 A | 8/1990 | Peake et al. | |
| 6,358,887 B1 | 3/2002 | Fischer et al. | |
| 6,548,451 B1 | 4/2003 | Wagner et al. | |
| 8,222,430 B2 * | 7/2012 | Kutose et al. ................ | 549/28 |

FOREIGN PATENT DOCUMENTS

| | | |
|---|---|---|
| DE | 19961465 A1 | 7/2000 |
| JP | 11-500114 A | 1/1999 |
| JP | 11-199410 A | 7/1999 |
| JP | 2002-509917 A | 4/2002 |
| JP | 2006-117604 A | 5/2006 |
| WO | WO 98/13361 A1 | 4/1998 |
| WO | WO 2008/152091 A2 | 12/2008 |

OTHER PUBLICATIONS

O'Mant et al., "The Preparation and Chemical Properties of 3-Acyl-5-arylidene-4-hydroxy-2,5-dihydro-2-oxothiophens, a New Class of Immunosuppressive Agent," Journal of the Chemical Society [Section] C: Organic, 1968, 12:1501-1505.

Sakamoto et al., "Photochemical Isomerization of O-Allyl and O-But-3-enyl Thiocarbamates," J. Chem. Soc. Perkin Trans. 1, 1995, 373-377.

Takahata et al., "Novel Synthesis of 2-Aminothiophenes via Iodoiminothiolactonization of γ,δ- Unsaturated Secondary Thioamides," Journal of the Chemical Society, Chemical Communications, 1986, 22:1671, Scheme 1, formula (3).

Xiong et al., "A Divergent Synthesis of γ-Iminolactones, Dihydroquinolin-2-ones, and γ-Lactames from β-Hydroxymethylcyclopropanylamides," J. Org. Chem., 2007, 72:8005-8009.

European Search Report dated May 16, 2012, in EP 09833217.4.

(Continued)

*Primary Examiner* — Golam M M Shameem
(74) *Attorney, Agent, or Firm* — Foley & Lardner LLP

(57) ABSTRACT

The present invention provides a pest control agent having a novel skeleton, which can be synthesized industrially, and also has excellent biological activity and residual effects. Specifically, the present invention provides a 1-heterodiene derivative represented by Formula (1) or a salt thereof, and a pest control agent including, as an active ingredient, a 1-heterodiene derivative or a salt thereof.

[Chemical Formula 1]

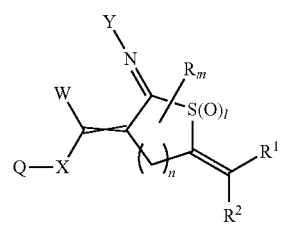

Formula (1)

6 Claims, No Drawings

(56) References Cited

OTHER PUBLICATIONS

International Search Report dated Mar. 16, 2010, in PCT/JP2009/006962.
Notice of Allowance dated Apr. 25, 2012, in U.S. Appl. No. 13/139,859.
Danishefsky et al., "Total Synthesis of Pretyrosine (Arogenate)," J. Am. Chem. Soc., 1981, 103:1602-1604.
Meyer et al., "1,5-Diaryl-2,3-pyrrolidinediones. VIII. Synthesis and Structure Proof," J. Org. Chem., 1957, 1554-1560.
Padwa et al., "Additive and Vinylogous Pummerer Reactions of Amido Sulfoxides and Their Use in the Preparation of Nitrogen Containing Heterocycles," J. Org. Chem., 1998, 63:4256-4268.
Tojino et al., "Cyclizative radical carbonylations of azaenynes ty TTMSS and hexanethiol leading to alpha-silyl- and thiomethylene lactams. Insights into the E/Z stereoselectivities," Org. Biomol. Chem., 2003, 1:4262-4267.
Tojino et al., "Cyclizative radical carbonylations of azaenynes by TTMSS and hexanethiol leading to alpha-silyl- and thiomethylene lactams. Insights into the E/Z stereoselectivities," Org. Biomol. Chem., 2003, 1:4262-4267.

* cited by examiner

1-HETERODIENE DERIVATIVE AND PEST CONTROL AGENT

TECHNICAL FIELD

The present invention relates to a novel 1-heterodiene derivative or a salt thereof, and a pest control agent containing, as an active ingredient, at least one selected amongst 1-heterodiene derivatives, and to a salt thereof.

This application is a National Stage application of PCT/JP2010/069915, filed Nov. 9, 2010, which claims priority from Japanese Patent Application No. 2009-258651, filed on Nov. 12, 2009, the disclosure of which is incorporated by reference herein.

BACKGROUND ART

Numerous compounds having insecticidal and acaricidal activity are known. However, problems still exist, such as ineffectivness, limitations regarding use due to drug resistance-related problems, pesticide injury problems, and strong toxicity to people, animals, and fish, and the like.

As compounds having a skeleton similar to that of the compound of the present invention, Non-Patent Literature 1 describes a compound represented by Formula (2), and Non-Patent Literature 2 describes a compound represented by Formula (3). However, the bioactivity of the compounds described in these non-patent literatures is unclear.

[Chemical Formula 1]

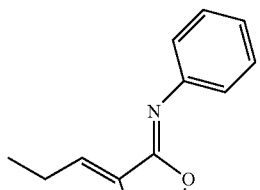

Formula (2)

[Chemical Formula 2]

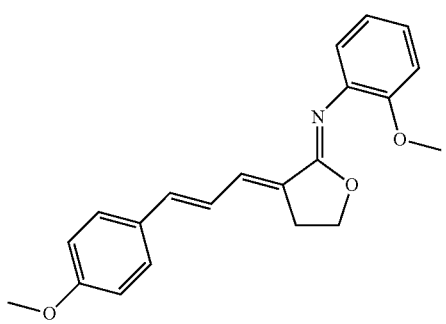

Formula (3)

CITATION LIST

Non-Patent Literature

[Non-Patent Literature 1]
J. Chem. Soc., Perkin Trans 1, 1995, 373-377
[Non-Patent Literature 2]
J. Org. Chem., 72, 8005-8009 (2007)

SUMMARY OF INVENTION

Technical Problem

An object of the present invention is to provide a 1-heterodiene derivative having a novel skeleton, which can be synthesized industrially and also has excellent biological activity and residual effects, or a salt thereof, and a pest control agent.

Solution to Problem

The present inventors have intensively studied so as to achieve the object mentioned above and found that a 1-heterodiene derivative having a specific structure, or a salt thereof has excellent insecticidal and acaricidal activity, and thus the present invention has been completed.

Namely, the present invention includes the following.

<1> A 1-heterodiene derivative represented by Formula (1):

[Chemical Formula 3]

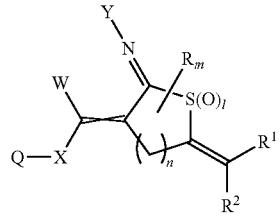

Formula (1)

wherein Q in Formula (1) represents a non-substituted or substituted C1-6 alkyl group, a non-substituted or substituted C2-6 alkenyl group, a non-substituted or substituted C2-6 alkynyl group, a non-substituted or substituted C3-8 cycloalkyl group, a non-substituted or substituted C4-8 cycloalkenyl group, a non-substituted or substituted C6-10 aryl group, or a non-substituted or substituted heterocyclic group;

W represents a hydrogen atom, or a non-substituted or substituted C1-6 alkyl group;

Y represents a non-substituted or substituted C6-10 aryl group, a non-substituted or substituted C3-8 cycloalkyl group, or a non-substituted or substituted heterocyclic group;

X represents an oxygen atom, a sulfur atom, a sulfinyl group, or a sulfonyl group;

l represents the number of oxygen atoms in parenthesis and is any one integer of 0 to 2;

n represents the repeat number of methylene groups in parenthesis and is any one integer of 1 to 4;

R represents a non-substituted or substituted C1-6 alkyl group, a non-substituted or substituted C2-6 alkenyl group, a non-substituted or substituted C2-6 alkynyl group, non-substituted or substituted C3-8 cycloalkyl group, a non-substituted or substituted C4-8 cycloalkenyl group, a non-substituted or substituted C6-10 aryl group, or a non-substituted or substituted heterocyclic group;

m represents the number of R(s) and is any one integer of 0 to 8 and, when m is 2 or more, R may be the same or different, and also any plural R (s) may be combined to form a non-substituted or substituted 3- to 8-membered ring;

$R^1$ and $R^2$ each independently represents a hydrogen atom, a non-substituted or substituted C1-6 alkyl group, or a non-substituted or substituted C3-8 cycloalkyl group, and $R^1$ and $R^2$ may be combined to form a non-substituted or substituted 3- to 8-membered ring; and an E-isomer, a Z-isomer, or a mixture thereof is expressed by a carbon-carbon double stereo bond (Undefined Double Stereo Bonds) in Formula (1);
or a salt thereof.
<2> The 1-heterodiene derivative according to the above <1>, wherein n is 2, or a salt thereof.
<3> The 1-heterodiene derivative according to the above <1> or <2>, wherein Q is a non-substituted or substituted C6-10 aryl group, or a non-substituted or substituted heterocyclic group, or a salt thereof.
<4> The 1-heterodiene derivative according to any one of the above <1> to <3>, wherein Y is a non-substituted or substituted C6-10 aryl group, or a salt thereof.
<5> A pest control agent comprising, as an active ingredient, at least one selected from the 1-heterodiene derivative according to any one of the above <1> to <4> and a salt thereof.
<6> The pest control agent according to the above <5>, wherein the pest is an insect or acarid.

Advantageous Effects of Invention

According to the present invention, it is possible to provide a 1-heterodiene derivative having a novel structure or a salt thereof. The present invention can also provide a pest control agent including, as an active ingredient, the 1-heterodiene derivative or a salt thereof, which has excellent biological activity, particularly excellent biological activity against insects and acarids, and also has high safety.

DESCRIPTION OF EMBODIMENTS

The 1-heterodiene derivative according to the present invention is a compound represented by Formula (1) mentioned above. Each group in Formula (1) will be described in detail below. As used herein, "Ca-b - - - group" and "Cc - - - group" mean that the numbers of carbon atoms constituting the groups are "a to b" and "c".

"which has a substituent" means that any one hydrogen atom in the "group" serving as a mother nucleus is substituted with a group having a structure which is different from that of the mother nucleus. There is no particular limitation on the number of the "substituent".

Examples of the "substituent" include "C1-6 alkyl group", "C2-6 alkenyl group", "C2-6 alkynyl group", "C3-8 cycloalkyl group", "C4-8 cycloalkenyl group", "C6-10 aryl group", "heterocyclic group", "C1-11 acyl group", "(1-imino)C1-6 alkyl group", "C1-6 alkoxy group", "halogen atom", "silyl group", "hydroxyl group", "amino group", "thiol group", "sulfinyl group", "sulfonyl group", "cyano group", "nitro group", "formyl group", "C1-6 haloalkyl group", "aryloxy group", or "C7-12 aralkyl group" defined below. In these "substituents", any one hydrogen atom in the above "substituent" may be substituted with the other "substituent".

Q in Formula (1) represents a non-substituted or substituted C1-6 alkyl group, a non-substituted or substituted C2-6 alkenyl group, a non-substituted or substituted C2-6 alkynyl group, a non-substituted or substituted C3-8 cycloalkyl group, a non-substituted or substituted C4-8 cycloalkenyl group, a non-substituted or substituted C6-10 aryl group, or a non-substituted or substituted heterocyclic group.

In Q in Formula (1), the "non-substituted C1-6 alkyl group" is a linear or branched saturated hydrocarbon group of 1 to 6 carbon atoms. Examples thereof include a methyl group, an ethyl group, an n-propyl group, an i-propyl group, an n-butyl group, an s-butyl group, an i-butyl group, a t-butyl group, an n-pentyl group, an n-hexyl group and the like.

Examples of the "C1-6 alkyl group having a substituent" include "C1-6 alkyl group" having a "C3-6 cycloalkyl group" as a substituent (i.e., "C3-6 cycloalkyl C1-6 alkyl group", and preferably "C3-6 cycloalkyl C1-2 alkyl group") such as a cyclopropylmethyl group, a 2-cyclopropylethyl group, a cyclopentylmethyl group, and a 2-cyclohexylethyl group; "C1-6 alkyl groups" having "C4-6 cycloalkenyl group" as a substituent (i.e., "C4-6 cycloalkenyl C1-6 alkyl group", and preferably "C4-6 cycloalkenyl C1-2 alkyl group") such as a cyclopentenylmethyl group, a 3-cyclopentenylmethyl group, a 3-cyclohexenylmethyl group, and a 2-(3-cyclohexenyl)ethyl group; "C1-6 alkyl groups" having a "halogeno group" as a substituent (i.e., "C1-6 haloalkyl group", preferably "C1-6 haloalkyl group substituted with 1 to 3 halogen atoms", particularly preferably a trifluoromethyl group) such as a fluoromethyl group, a chloromethyl group, a bromomethyl group, a difluoromethyl group, a dichloromethyl group, a dibromomethyl group, a trifluoromethyl group, a trichloromethyl group, a tribromomethyl group, a 2,2,2-trifluoroethyl group, a 2,2,2-trichloroethyl group, a pentafluoroethyl group, a 4-fluorobutyl group, a 4-chlorobutyl group, a 3,3,3-trifluoropropyl group, a 2,2,2-trifluoro-1-trifluoromethylethyl group, a perfluorohexyl group, a perchlorohexyl group, and a 2,4,6-trichlorohexyl group; "C1-6 alkyl groups" having a "C6-10 aryl group" as a substituent (i.e., "C6-10 aryl C1-6 alkyl group", and preferably "phenyl C1-2 alkyl group") such as a benzyl group, a phenethyl group, a 3-phenylpropyl group, a 1-naphthylmethyl group, and a 2-naphthylmethyl group; "C1-6 alkyl groups" having a "heterocyclic group" as a substituent (i.e., "heterocyclic C1-6 alkyl group", and preferably "5- to 6-membered heterocyclic C1-2 alkyl group") such as 2-pyridylmethyl group, a 3-pyridylmethyl group, a 4-pyridylmethyl group, a 2-(2-pyridyl)ethyl group, a 2-(3-pyridyl)ethyl group, a 2-(4-pyridyl)ethyl group, a 3-(2-pyridyl)propyl group, a 3-(3-pyridyl)propyl group, a 3-(4-pyridyl)propyl group, a 2-pyrazylmethyl group, a 3-pyrazylmethyl group, a 2-(2-pyrazyl)ethyl group, a 2-(3-pyrazyl)ethyl group, a 3-(2-pyrazyl)propyl group, a 3-(3-pyrazyl)propyl group, a 2-pyrimidylmethyl group, a 4-pyrimidylmethyl group, a 2-(2-pyrimidyl)ethyl group, a 2-(4-pyrimidyl)ethyl group, a 3-(2-pyrimidyl)propyl group, a 3-(4-pyrimidyl)propyl group, a 2-furylmethyl group, a 3-furylmethyl group, a 2-(2-furyl)ethyl group, a 2-(3-furyl)ethyl group, a 3-(2-furyl)propyl group, and a 3-(3-furyl)propyl group; "C1-6 alkyl groups" having a "hydroxyl group" as a substituent (i.e., "hydroxy C1-6 alkyl group", and preferably "hydroxy C1-2 alkyl group") such as a hydroxymethyl group, a hydroxyethyl group, and hydroxypropyl group; and the like.

Examples of the "C1-6 alkyl group having a substituent" in which any one hydrogen atom in the above substituent is substituted with the other "substituent" include "hydroxy C1-6 alkyl groups" having a "C1-6 alkyl group" as a substituent (i.e., "C1-6 alkoxy C1-6 alkyl group", and preferably "C1-6 alkoxy C1-2 alkyl group") such as a methoxymethyl group, an ethoxymethyl group, a methoxyethyl group, an ethoxyethyl group, a methoxy-n-propyl group, an ethoxymethyl group, an ethoxyethyl group, an n-propoxymethyl group, an i-propoxyethyl group, an s-butoxymethyl group, a t-butoxyethyl group, a 1,2-dimethoxyethyl group, and a 2,2-dimethoxyethyl group; "C1-6 alkyl groups" having an "oxy group" as a substituent, such as an epoxy group and a 2,3-epoxypropyl group; "hydroxy C1-6 alkyl group" having a "C1-11 acyl group" as a substituent (i.e., "C1-11 acyloxy C1-6 alkyl group", and preferably "C2-7 acyloxy C1-2 alkyl group") such as a formyloxymethyl group, an acetoxymethyl group, a 2-acetoxyethyl group, a propionyloxymethyl group, and a propionyloxyethyl group; and the like.

In Q in Formula (1), the "non-substituted C2-6 alkenyl group" is a linear or branched unsaturated hydrocarbon group of 2 to 6 carbon atoms, which has at least one carbon-carbon double bond. Examples thereof include a vinyl group, a 1-propenyl group, a allyl group, a 1-butenyl group, a 2-butenyl group, a 3-butenyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group, a 5-hexenyl group, a 1-methyl-2-propenyl group, a 2-methyl-2-propenyl group, a 1-methyl-2-butenyl group, a 2-methyl-2-butenyl group and the like. Among these groups, a C2-4 alkenyl group is preferable.

Examples of the "C2-6 alkenyl group having a substituent" include "C2-6 alkenyl groups" having a "halogeno group" as a substituent (i.e., "C2-6 haloalkenyl group", and preferably "C2-6 haloalkenyl group substituted with 1 to 3 halogen atoms") such as a 3-chloro-2-propenyl group, a 4-chloro-2-butenyl group, a 4,4-dichloro-3-butenyl group, a 4,4-difluoro-3-butenyl group, a 3,3-dichloro-2-propenyl group, a 2,3-dichloro-2-propenyl group, a 3,3-difluoro-2-propenyl group, a 2,4,6-trichloro-2-hexenyl group and the like.

In Q in Formula (1), the "non-substituted C2-6 alkynyl group" is a linear or branched unsaturated hydrocarbon group of 2 to 6 carbon atoms, which has at least one carbon-carbon triple bond. Examples thereof include an ethynyl group, a 1-propynyl group, a propargyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 1-methyl-2-propynyl group, a 2-methyl-3-butynyl group, a 1-methyl-2-butynyl group, a 2-methyl-3-pentynyl group, a 1,1-dimethyl-2-butynyl group and the like. Among these groups, a C2-4 alkynyl group is preferable.

Examples of the "C2-6 alkynyl group having a substituent" include "C2-6 alkynyl groups" having a "halogeno group" as a substituent (i.e., "C2-6 haloalkynyl group", and preferably "C2-6 haloalkynyl group substituted with 1 to 3 halogen atoms") such as a 3-chloro-1-propynyl group, a 3-chloro-1-butynyl group, a 3-bromo-1-butynyl group, a 3-bromo-2-propynyl group, a 3-iodo-2-propynyl group, a 3-bromo-1-hexynyl group, a 5,5-dichloro-2-methyl-3-pentynyl group, a 4-chloro-1,1-dimethyl-2-butynyl group and the like.

In Q in Formula (1), the "non-substituted C3-8 cycloalkyl group" is a saturated hydrocarbon group of 3 to 8 carbon atoms, which has a cyclic moiety. Examples thereof include a cyclopropyl group, a cyclobutyl group, a cyclopentyl group, a cyclohexyl group and the like.

Examples of the "C3-8 cycloalkyl group having a substituent" include "C3-8 cycloalkyl group" having a "C1-6 alkyl group" as a substituent (i.e., "C1-6 alkyl C3-8 cycloalkyl group", and preferably "C4-8 cycloalkyl group substituted with 1 to 3 C1-2 alkyl groups") such as a 2,3,3-trimethylcyclobutyl group, a 4,4,6,6-tetramethylcyclohexyl group, a 1,3-dibutylcyclohexyl group and the like.

In Q in Formula (1), the "non-substituted C4-8 cycloalkenyl group" is an alkenyl group of 4 to 8 carbon atoms, which has a cyclic moiety. Examples thereof include a 1-cyclobutenyl group, a 1-cyclopentenyl group, a 3-cyclopentenyl group, a 1-cyclohexenyl group, a 3-cyclohexenyl group, a 3-cycloheptenyl group, a 4-cyclooctenyl group and the like.

Examples of the "C4-8 cycloalkenyl group having a substituent" include "C4-8 cycloalkenyl group" having a "C1-6 alkyl group" as a substituent (i.e., "C1-6 alkyl C4-8 cycloalkenyl group", and preferably "C4-6 cycloalkenyl group substituted with 1 to 3 C1-2 alkyl groups") such as a 2-methyl-3-cyclohexenyl group, a 3,4-dimethyl-3-cyclohexenyl group and the like.

In Q in Formula (1), the "non-substituted C6-10 aryl group" is a monocyclic or polycyclic aryl group of 6 to 10 carbon atoms. In the polycyclic aryl group, when at least one ring is an aromatic ring, the remaining ring may be any of a saturated hydrocarbon ring, an unsaturated hydrocarbon ring or an aromatic hydrocarbon ring. Examples thereof include a phenyl group, a naphthyl group, an azulenyl group, an indenyl group, an indanyl group, a tetralinyl group and the like. Among these groups, a phenyl group is preferable.

Examples of the "C6-10 aryl group having a substituent" include a 2-chlorophenyl group, a 4-hydroxyphenyl group and the like.

In Q in Formula (1), "non-substituted heterocyclic group" is a group having a 3- to 7-membered ring, which has, as atoms constituting the ring, 1 to 4 heteroatoms selected from a nitrogen atom, an oxygen atom and a sulfur atom, in addition to a carbon atom. Examples thereof include a group having an aromatic heterocycle, a saturated heterocycle, an unsaturated heterocycle, or a fused heterocycle of these heterocycles with a benzene ring. More specific examples thereof include an aziridin-1-yl group, an aziridin-2-yl group; a tetrahydrofuran-2-yl group, a tetrahydrofuran-3-yl group, a pyrrolidin-1-yl group, a pyrrolidin-2-yl group, a pyrrolidin-3-yl group; pyrrol-1-yl group, a pyrrol-2-yl group, a pyrrol-3-yl group, a furan-2-yl group, a furan-3-yl group, a thiophen-2-yl group, a thiophen-3-yl group, a imidazol-1-yl group, an imidazol-2-yl group, an imidazol-4-yl group, an imidazol-5-yl group, a pyrazol-1-yl group, a pyrazol-3-yl group, a pyrazol-4-yl group, a pyrazol-5-yl group, an oxazol-2-yl group, an oxazol-4-yl group, an oxazol-5-yl group, a thiazol-2-yl group, a thiazol-4-yl group, a thiazol-5-yl group, an isoxazol-3-yl group, an isoxazol-4-yl group, an isoxazol-5-yl group, an isothiazol-3-yl group, an isothiazol-4-yl group, an isothiazol-5-yl group, a 1,2,3-triazol-1-yl group, a 1,2,3-triazol-4-yl group, a 1,2,3-triazol-5-yl group, a 1,2,4-triazol-1-yl group, a 1,2,4-triazol-3-yl group, a 1,2,4-triazol-5-yl group, a 1,3,4-oxadiazol-2-yl group, a 1,2,4-oxadiazol-3-yl group, a 1,3,4-thiadiazol-2-yl group, a 1,2,4-thiadiazol-3-yl group, a tetrazol-1-yl group, a tetrazol-2-yl group; pyridin-2-yl group, a pyridin-3-yl group, a pyridin-4-yl group, a pyrazin-2-yl group, a pyrimidin-2-yl group, a pyrimidin-4-yl group, a pyrimidin-5-yl group, a pyridazin-3-yl group, a pyridazin-4-yl group, a triazinyl group; an indol-1-yl group, an indol-2-yl group, an indol-3-yl group, an indol-4-yl group, an indol-5-yl group, an indol-6-yl group, an indol-7-yl group, a benzofuran-2-yl group, a benzofuran-3-yl group, a benzofuran-4-yl group, a benzofuran-5-yl group, a benzofuran-6-yl group, a benzofuran-7-yl group, a benzothiophen-2-yl group, a benzothiophen-3-yl group, a benzothiophene-4-yl group, a benzothiophen-5-yl group, a benzothiophen-6-yl group, a benzothiophen-7-yl group, an isoindol-1-yl group, an isoindol-2-yl group, an isoindol-4-yl group, an isoindol-5-yl group, an isoindol-6-yl group, an isoindol-7-yl group, an isobenzofuran-1-yl group, an isobenzofuran-4-yl group, an isobenzofuran-5-yl group, an isobenzofuran-6-yl group, an isobenzofuran-7-yl group, a benzoimidazol-1-yl group, a benzoimidazol-2-yl group, a benzoimidazol-4-yl group, a benzoimidazol-5-yl group, a benzoxazol-2-yl group, a benzoxazol-4-yl group, a benzoxazol-5-yl group, a benzothiazol-2-yl group, a benzothiazol-4-yl group, a benzothiazol-5-yl group; chromen-2-yl group, a chromen-3-yl group, a chromen-4-yl group, a chromen-5-yl group, a chromen-6-yl group, a chromen-7-yl group, a chromen-8-yl group, a quinolin-2-yl group, a quinolin-3-yl group, a quinolin-4-yl group, a quinolin-5-yl group, a quinolin-6-yl group, a quinolin-7-yl group, a quinolin-8-yl group, an isoquinolin-1-yl group, an isoquinolin-3-yl group, an isoquinolin-4-yl group, an isoquinolin-5-yl group, an isoquinolin-6-yl group, an isoquinolin-7-yl group, an isoquinolin-8-yl group; a piperidin-1-yl group, a piperidin-2-yl group, a piperidin-3-yl group, a piperidin-4-yl group, a piperazin-1-yl group, a piperazin-2-yl group, a piperazin-3-yl group, a morpholin-2-yl group, a morpholin-3-yl group, a morpholin-4-yl group; 1,3-benzodioxol-4-yl group, a 1,3-benzodioxol-5-yl group, a 1,4-benzodioxan-5-yl group, a 1,4-benzodioxan-6-yl group, a 3,4-dihydro-2H-1,5-benzodioxepin-6-yl group, a 3,4-dihydro-2H-1,5-benzodioxepin-7-yl group, a 2,3-dihydrobenzofuran-4-yl group, a 2,3-dihydrobenzofuran-5-yl group, a 2,3-dihydrobenzofuran-6-yl group, a 2,3-dihydrobenzofuran-7-yl group; and the like.

Among these groups, a 5- to 7-membered heterocyclic group is preferable, and a pyrazol-1-yl group, a pyrazol-3-yl group, a pyrazol-4-yl group, a pyrazol-5-yl group, a pyridin-2-yl group, a pyridin-3-yl group, a pyridin-4-yl group, a pyrazin-2-yl group and a pyrazin-3-yl group are particularly preferable.

Examples of the "heterocyclic group having a substituent" include a 5-pyrazolon-1-yl group, a 5-pyrazolon-3-yl group, a 5-pyrazolon-4-yl group, a 3,5-dimethylpyrazol-1-yl group, a 3,5-dimethylpyrazol-4-yl group, a chloropyridin-2-yl group, a chloropyridin-3-yl group, a chloropyridin-4-yl group, a hydroxypyridin-2-yl group, a hydroxychloropyridin-3-yl group, a hydroxypyridin-4-yl group, a 2,5-dimethylpyrazin-3-yl group, a 2,5-dimethylpyrazin-6-yl group and the like.

In Formula (1), W represents a hydrogen atom, or a non-substituted or substituted C1-6 alkyl group.

In W in Formula (1), examples of the "non-substituted or substituted C1-6 alkyl group" include the respective groups which are the same as described in Q.

In Formula (1), Y represents a non-substituted or substituted C6-10 aryl group, a non-substituted or substituted C3-8 cycloalkyl group, or a non-substituted or substituted heterocyclic group.

Examples of the non-substituted or substituted C6-10 aryl group, non-substituted or substituted C3-8 cycloalkyl group, or non-substituted or substituted heterocyclic group in Y include the respective groups which are the same as described in Q.

In Formula (1), X represents an oxygen atom, a sulfur atom, a sulfinyl group, or a sulfonyl group.

l represents the number of oxygen atoms in parenthesis and is any one integer of 0 to 2.

n represents the repeat number of methylene groups in parenthesis and is any one integer of 1 to 4.

In Formula (1), R represents a non-substituted or substituted C1-6 alkyl group, a non-substituted or substituted C2-6 alkenyl group, a non-substituted or substituted C2-6 alkynyl group, a non-substituted or substituted C3-8/cycloalkyl group, a non-substituted or substituted C4-8 cycloalkenyl group, a non-substituted or substituted C6-10 aryl group, or a non-substituted or substituted heterocyclic group.

Examples of the non-substituted or substituted C1-6 alkyl group, non-substituted or substituted C2-6 alkenyl group, non-substituted or substituted C2-6 alkynyl group, non-substituted or substituted C3-8 cycloalkyl group, non-substituted or substituted C4-8 cycloalkenyl group, non-substituted or substituted C6-10 aryl group, or non-substituted or substituted heterocyclic group in R include the respective groups which are the same as described in Q.

m represents the number of R (s) and is any one integer of 0 to 8. When m is 2 or more, R may be the same or different. Any plural R (s) may be combined to form a non-substituted or substituted 3- to 8-membered ring. Examples of the non-substituted or substituted 3- to 8-membered ring to be formed by combining R(s) include a saturated hydrocarbon ring, an unsaturated hydrocarbon ring, an aromatic hydrocarbon ring, a saturated heterocycle, an unsaturated heterocycle or an aromatic heterocycle. Also, this 3- to 8-membered ring and a non-substituted or substituted aromatic hydrocarbon ring or aromatic heterocycle may be combined to form a fused ring. Examples of the fused ring include a tetrahydronaphthalene ring, indane ring, a tetrahydroisoquinoline ring, a tetrahydrobenzofuran ring, a 1,2-benzoisothiazole ring, a cyclopentapyrimidine ring and the like.

In Formula (1), $R^1$ and $R^2$ each independently represents a hydrogen atom, a non-substituted or substituted C1-6 alkyl group, or a non-substituted or substituted C3-8 cycloalkyl group. $R^1$ and $R^2$ may be combined to form a non-substituted or substituted 3- to 8-membered ring.

Examples of the non-substituted or substituted C1-6 alkyl group, and non-substituted or substituted C3-8 cycloalkyl group in $R^1$ and $R^2$ include the respective groups which are the same as described in Q.

Examples of the non-substituted or substituted 3- to 8-membered ring to be formed by combining $R^1$ and $R^2$ include the non-substituted or substituted 3- to 8-membered ring to be formed by combining R(s) which is the same as described in R.

Salts of the 1-heterodiene derivative according to the present invention are agrihorticulturally acceptable salts of the compound represented by Formula (1). Examples thereof include salts of inorganic acids such as hydrochloric acid, sulfuric acid and tetrafluoroboric acid; salts of organic acids such as acetic acid and lactic acid; salts of alkali metals such as lithium, sodium and potassium; salts of alkali earth metals such as calcium and magnesium; salts of transition metals such as iron and copper; salts of organic bases such as ammonia, triethylamine, tributylamine, pyridine and hydrazine; and the like.

The 1-heterodiene derivative according to the present invention and a salt thereof (hereinafter sometimes referred to as a "compound of the present invention") will be more specifically described below by way of Production Examples of the 1-heterodiene derivative represented by Formula (1). The below-mentioned Production Examples are for illustrative purpose only and they do not limit the scope of the invention.

[Chemical Formula 4]

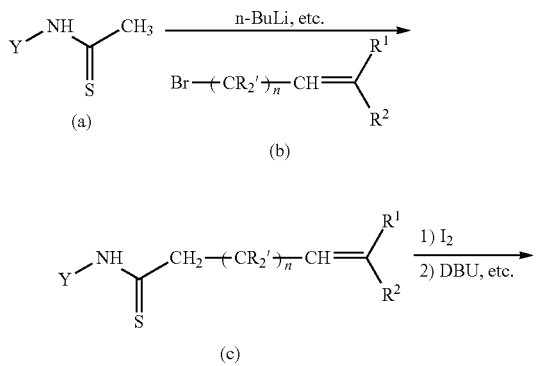

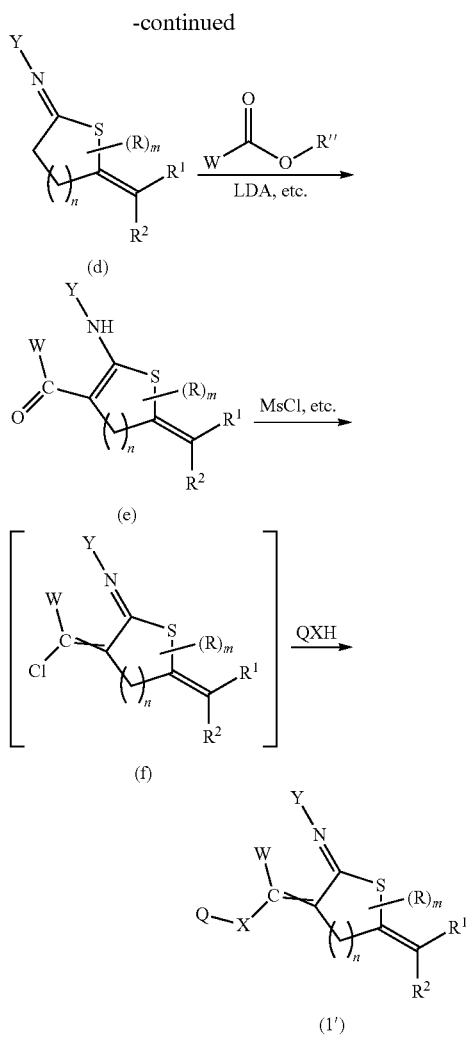

In the reaction scheme mentioned above, Q, W, Y, n, R, m, R$^1$ and R$^2$ have the same meanings as those in Formula (1). R' represents a hydrogen atom or R. R" represents an alkyl group.

The compound represented by Formula (1') can be synthesized, by example, by the following manner.

First, a compound represented by Formula (a) is reacted with a compound represented by Formula (b) in the presence of an organolithium compound such as n-butyllithium to synthesize a compound represented by Formula (c). Then, iodine is added to form a ring, followed by deiodination with a base such as diazabicycloundecene to obtain a compound represented by Formula (d). An ester compound is added thereto in the presence of a base such as lithiumdiisopropylamide to obtain a compound represented by Formula (e). Then, the compound is reacted with mesyl chloride or tosyl chloride to give a compound represented by Formula (f), and thus a compound represented by Formula (1') can be obtained by adding thiol, alcohol, phenol or the like In any reaction, if purification of the product is required after completion of the reaction and subsequent ordinary after-treatment operations, the target compound may be isolated by purification using conventionally known means such as distillation, recrystallization, or column chromatography.

The structure of the target compound can be identified and confirmed by known analysis means such as elemental analysis, NMR spectroscopy, IR spectroscopy and MS spectroscopy.

Since the compounds of the present invention have adulticidal, nymphicidal, larvicidal and ovicidal activities, they can be used for controlling crop-damaging insects, acarids, sanitary insects, stored grain pest insects, clothes pests, household pests and the like. Specific organisms to be the target of control include the following.

Pests which belong to the order of Lepidoptera such as *Spodoptera litura*, *Mamestra brassicae*, *Agrotis ipsilon*, green caterpillars, *Autographa nigrisigna*, *Plutella xylostella*, *Adoxophyes honmai*, *Homona magnanima*, *Carposina sasakii*, *Grapholita molesta*, *Phyllocnistis citrella*, *Caloptilia theivora*, *Phyllonorycter ringoniella*, *Lymantria dispar*, *Euproctis pseudoconspersa*, *Chilo suppressalis*, *Cnaphalocrocis medinalis*, *Ostrinia nubilasis*, *Hyphantria cunea*, *Cadra cautella*, genus *Heliothis*, genus *Helicoverpa*, genus *Agrothis*, *Tinea translucens*, *Cydia pomonella*, and *Pectinophora gossypiella*; pests which belong to the order of Hemiptera such as *Myzus persicae*, *Aphis gossypii*, *Lipaphis erysimi*, *Rhopalosiphum padi*, *Riptortus clavatus*, *Nezara antennata*, *Unaspis yanonensis*, *Pseudococcus comstocki*, *Trialeurodes vaporariorum*, *Bemisia tabaci*, *Bemisia argentifolii*, *Psylla pyrisuga*, *Stephanitis nashi*, *Nilaparuata lugens*, *Laodelphax stratella*, *Sogatella furcifera*, and *Nephotettix cincticeps*; pests which belong to the order of Coleoptera such as *Phyllotreta striolata*, *Aulacophora femoralis*, *Leptinotarsa decemlineata*, *Lissorhoptrus oryzophilus*, *Sitophilis zeamais*, *Callosobruchus chinensis*, *Popillia japonica*, *Anomala rufocuprea*, genus *Diabrotica*, *Lasioderma serricorne*, *Lyctus brunneus*, *Monochamus alternatus*, *Anoplophora malasiaca*, genus *Agriotis*, *Epilachna vigintioctopunctata*, *Tenebroides mauritanicus*, and *Anthonomus grandis*; pests which belong to the order of Diptera such as *Musca domestica*, *Calliphora lata*, *Boettcherisca peregrine*, *Zeugodacus cucurbitae*, *Bactrocera dorsalis*, *Delia platura*, *Agromyza oryzae*, *Drosophila melanogaster*, *Stomoxys calcitrans*, *Culex tritaeniorhynchus*, *Aedes aegypti*, and *Anopheles sinensis*; pests which belong to the order of Thysanoptera such as *Thrips palmi* and *Scirtothrips dorsalis*; pests which belong to the order of Hymenoptera such as *Monomorium pharaonis*, *Vespa simillima xanthoptera*, and *Athalia rosae ruficornis*; pests which belong to the order of Orthoptera such as *Locusta migratoria*, *Blattella germanica*, *Periplaneta americana*, and *Periplaneta fuliginosa*; pests which belong to the order of Isoptera such as *Coptotermes formosanus* and *Reticulitermes speratus speratus*; pests which belong to the order of Siphonaptera such as *Pulex irritans* and *Ctenocephalides felis*; pests which belong to the order of Phthiraptera such as *Pediculus humanus*; Acarina such as *Tetranychus urticae*, *Tetranychus cinnabarinus*, *Tetranychus kanzawai*, *Panonychus citri*, *Panonychus ulmi*, *Aculops pelekassi*, *Aculus schlechtendali*, *Polyphagotarsonemus latus*, genus *Brevipalpus*, genus *Eotetranichus*, *Rhizoglyphus robini*, *Tyrophagus putrescentiae*, *Dermatophagoides farinae*, *Boophilus microplus*, and *Haemaphysalis longicornis*; and plant parasitic nematodes such as *Meloidogyne incognita*, *Pratylenchus* spp., *Heterodera glycines*, *Aphelenchoides besseyi*, and *Bursaphelenchus xylophilus*.

Pests to which the present invention is preferably applied are pests which belong to the order of Lepidoptera, pests which belong to the order of Hemiptera, Acarina, pests which belong to the order of Thysanoptera, and pests which belong to the order of Coleoptera.

Moreover, drugs which are also effective for pests or Acarnia that are of resistant lineage are desired since in recent years, resistance to organophosphorus pesticides, carbamate pesticides, or acaricides developed among many pests such as *Plutella xylostella*, *Delphacidae*, *Deltocephalidae*, and *Aphi-*

*didae* has caused problems because of insufficient effects of these drugs. The compounds of the present invention are drugs having excellent insecticidal and acaricidal effects not only on those of sensitive lineages but also on pests of lineages resistant to organophosphorus pesticides, carbamate pesticides, and pyrethroid pesticides, and on Acarnia of lineages resistant to acaricides.

Additionally, the compounds of the present invention are drugs that show less herbicide injuries, have lower toxicity to fish and warm-blooded animals, and higher safety.

The pest control agent according to the present invention contains the compound represented by Formula (1) of the present invention as an active ingredient. The compound represented by Formula (1) of the present invention can be used alone, or two or more kinds of them can be used in combination. The compounds of the present invention may be directly used without adding other constituents in case of actually applying. However, they are generally used by mixing them with solid carriers, liquid carriers, or gaseous carriers, or by immersing them in substrates such as porous ceramic plates and nonwoven fabrics, followed by adding surfactants or other adjuvants, if needed, to formulate them, for using as pesticides, in forms of conventional pesticides such as wettable powders, granules, dusts, emulsifiable concentrates, water soluble powders, suspensions, granular wettable powders, flowable, aerosols, aerosols, heat-transpiration agents, fumigants, poison baits, and microcapsules.

When the compounds are used as solid agents, it is possible to use, as additives and carriers, vegetable powders such as soy bean grains and wheats; mineral impalpable powders such as diatomites, apatites, gypsums, talcs, bentonites, pyrophyllites, and clays; organic or inorganic compounds such as sodium benzoates, ureas, and mirabilite.

When the compounds are used as liquid agents, it is possible to use, as solvents, petroleum fractions such as kerosenes, xylene, and solvent naphthas; cyclohexanes, cyclohexanons, dimethylformamides, dimethylsulfoxides, alcohols, acetones, methyl isobutylketons, mineral oils, vegetable oils, water and the like.

It is possible to use, as gaseous carriers used for propellants, butane gases, LPG, dimethyl ethers, and carbonic acid gases.

It is possible to use, as substrates for poison baits, bait components such as cereal powders, vegetable oils, sugars, and crystalline celluloses; antioxidants such as dibutylhydroxytoluene and nordihydroguairetic acid; preservatives such as dehydroacetic acid; agents for preventing children or pets from eating them by mistake, such as powdered capsicums; flavors for attracting pest insects, such as cheese flavors and onion flavors.

If needed, surfactants may be added to these formulations so as to form their uniform and stable conformations. There is no particular limitation on surfactants, and examples thereof include nonionic surfactants such as alkyl ethers added with polyoxyethylenes, higher fatty acid esters added with polyoxyethylenes, sorbitan higher fatty acid esters added with polyoxyethylenes, and tristyrylphenyl ethers added with polyoxyethylenes; sulfuric ester salts of alkyl phenyl ethers added with polyoxyethylenes, alkylnaphthalene sulfonates, polycarboxylates, lignin sulfonates, formaldehyde condensates of alkylnaphthalene sulfonates, copolymers of isobutylene-maleic anhydrides and the like.

When the compounds of the present invention are used as pest control agents for farming, the amounts of their active ingredients in Formulation are from 0.01 to 90% by weight, and preferably from 0.05 to 85% by weight. The compounds may be used in the form of solutions, suspensions or emulsions by diluting with water to their predetermined concentrations, in case of wettable powders, emulsifiable concentrates, suspensions, flowable agents, water soluble powders and granular wettable powders, or they may be used by directly spraying over plants or soils in case of dusts and granules.

When the compounds of the present invention are used as pest control agents for preventing epidemics, they can be used by diluting them with water to their determined concentrations in case of emulsifiable concentrates, wettable powders, and flowable agents, and the compounds can be directly used in case of oil solutions, aerosols, aerosols, poison baits, and anti-mite sheets.

The compounds of the present invention can also be used as sanitary pest control agents, animal drugs and the like. When the compounds of the present invention are used as pest control agents for preventing animal external parasites of domestic animals such as cattle and pigs, or pets such as dogs and cats, formulations of the compounds of the present invention are generally used according to a method known in a veterinary art. Examples of the method include a method of administering them for systemic control by tablets, capsules, immersion liquids, mixtures with feeds, suppositories, and injections (intramuscular, subcutaneous, intravenous, intraperitoneal, etc.); a method of administering them for non-systemic control by spraying, pouring on, or spotting on oily or aqueous liquid formulations; and a method of wearing materials produced by molding resin formulations into suitable forms such as collars and ear tags. In this case, the compounds of the present invention are generally used at a rate of 0.01 to 1,000 mg per 1 kg of a host animal.

It goes without saying that the compounds of the present invention can be used alone for exerting their sufficient effects. However, they can also be mixed with, or used in combination with at least one of other pest control agents, fungicides, insecticides, acaricides, herbicides, plant growth regulators, synergists, fertilizers, soil conditioners, and animal feeds.

Typical examples of active ingredients of the fungicides, insecticides, acaricides, and plant growth regulators, which may be mixed with, or used in combination with the compounds of the present invention, are shown below.

<Fungicide>:
captan, folpet, thiuram, ziram, zineb, maneb, mancozeb, propineb, polycarbamate, chlorothalonil, quintozene, captafol, iprodione, procymidone, fluoroimide, mepronil, flutolanil, pencycuron, oxycarboxin, fosetyl-aluminum, propamocarb, triadimefon, triadimenol, propiconazole, dichlobutorazol, bitertanol, hexaconazol, microbutanil, flusilazole, etaconazole, fluotrimazole, flutriafen, penconazole, diniconazole, cyproconazole, fenarimol, triflumizole, prochloraz, imazalil, pefurazoate, tridemorph, fenpropimorph, triforine, buthiobate, pyrifenox, anilazine, polyoxin, metalaxyl, oxadixyl, furalaxyl, isoprothiolane, probenazole, pyrrolnitrin, blasticidin S, kasugamycin, balidamycin, dihydrostreptomycin sulfate, benomyl, carbendazim, thiophanate methyl, hymexazol, basic copper chloride, basic copper sulfate, fentin acetate, triphenyltin hydroxide, diethofencarb, qinomethionate, binapacryl, lecithin, sodium hydrogencarbonate, dithianon, dinocap, fenaminosulf, diclomezine, guazatine, dodine, IBP, edifenphos, mepanipyrim, ferimzone, trichlamide, methasulfocarb, fluazinam, ethoqinolac, dimethomorph, pyroquilon, tecloftalam, fthalide, phenazine oxide, thiabendazole, tricyclazole, vinclozolin, cymoxanil, cyclobutanil, guazatine, propamocarb hydrochloride, oxolinic acid, cyflufenamid, iminoctadine, kresoxim-methyl, triazine, fenhexamid, cyazofamid, cyprodinil, prothioconazole, fenbuconazole, trifloxystrobin, azoxystrobin, hexaconazole, imibenconazole, tebuconazole, difenoconazole, and carpropamid.

<Insecticides/Acaricides>:
organophosphate-based compounds such as profenofos, dichlorvos, fenamiphos, fenitrothion, EPN, diazinon, chlorpyrifos-methyl, acephate, prothiofos, fosthiazate, phosphocarb, cadusafos, disulfoton, chlorpyrifos, demeton-S-methyl, dimethoate, parathion, BRP, CVMP, CVP, CYAP, DEP, MPP, PAP, isoxathion, ethion, ethoprophos, quinalphos, chlorpyrifos, dimethylvinphos, vamidothion, pyraclofos, phosalone, malathion, monocrotophos, and AKD-3088; carbamate-based compounds such as carbaryl, propoxur, aldicarb, carbofuran, thiodicarb, methomyl, oxamyl, ethiofencarb, pirimicarb, fenobucarb, carbosulfan, benfuracarb, MIPC, MPMC, MTMC, alanycarb, pyridaphenthion, pirimiphosmethyl, fenothiocarb, furathiocarb, bendiocarb, and XMC; nereistoxin derivatives such as cartap, thiocyclam, and bensultap; organochlorine-based compounds such as dicofol, tetradifon, and endosulufan; organic metal-based compounds such as fenbutatin oxide; pyrethroid-based compounds such as fenvalerate, permethrin, cypermethrin, deltamethrin, cyhalothrin, tefluthrin, ethofenprox, fenpropathrin, bifenthrin, acrinathrin, allethrin, cycroprothrin, halfenprox, flucythrinate, and resmethrin; benzoylurea-based compounds such as diflubenzuron, chlorfluazuron, teflubenzuron, flufenoxuron, lufenuron, novaluron, bistrifluoron, noviflumuron, and triflumuron; juvenile hormone-like compounds such as methoprene, pyriproxyfen, and fenoxycarb; pyridazinone-based compounds such as pyridaben; pyrazole-based compounds such as fenpyroximate, fipronil, tebufenpyrad, ethiprole, tolfenpyrad, acetoprole, pyrafluprole, and pyriprole; neonicotinoids such as imidacloprid, nitenpyram, acetamiprid, thiacloprid, thiamethoxam, clothianidin, and dinotefuran; hydrazine-based compounds such as tebufenozide, methoxyfenozide, chromafenozide, and halofenozide; dinitro-based compounds; organosulfur compounds; urea-based compound; triazine-based compounds; hydazone-based compounds; other compounds such as flonicamid, buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, flufenerim, pyridalyl, spirodiclofen, bifenazate, spiromesifen, spirotetramat, propargite, clofentezine, fluacrypyrim, flubendiamide, cyflumetofen, cyenopyrafen, MNI-0101, fenazaquin, metaflumizone, amidoflumet, CL-900167, DCIP, phenisobromolate, benzomate, metaldehyde, chlorantraniliprole, cyantraniliprole, spinetoram, and pyrifluquinazon; antibiotics or semisynthetic antibiotics such as avermectin, emamectin-benzoate, milbemectin, spinosad, ivermectin, and lepimectin; natural products such as azadirachtin and rotenone; and microbial pesticides such as BT and entomopathogenic viruses, etomopathogenic fungi, and nematophagous fungi.

<Plant Growth Regulators>:
abscisic acid, indolebutyric acid, uniconazole, ethychlozate, ethephon, cloxyfonac, chlormequat, chlorella extract, calcium peroxide, cyanamide, dichlorprop, gibberellin, daminozide, decyl alcohol, trinexapac-ethyl, mepiquat-chloride, paclobutrazol, paraffin, wax, piperonyl butoxide, pyraflufen-ethyl, flurprimidol, prohydrojasmon, prohexadione-calcium, benzylaminopurine, pendimethalin, forchlorfenuron, maleic hydrazide potassium, 1-naphthylacetamide, 4-CPA, MCPB, choline, oxyquinoline sulfate, ethychlozate, butralin, 1-methylcyclopropene, and aviglycine hydrochloride.

EXAMPLES

The present invention will be described in further detail below by way of Examples, but the present invention is not limited to these Examples.

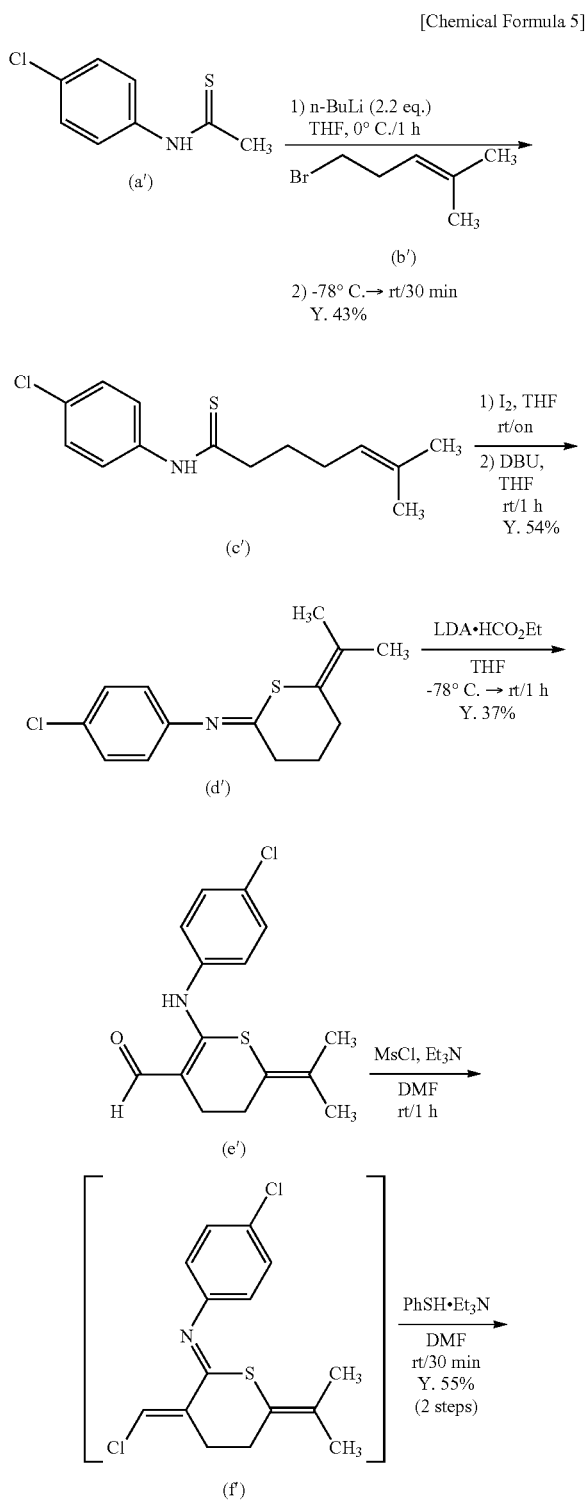

-continued

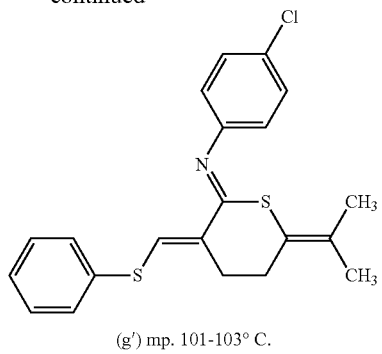

(g') mp. 101-103° C.

Example 1

(I) Synthesis of 6-methyl-5-heptenethioic acid (4-chloro-phenyl)-amide (Compound Represented by Formula (c'))

In a dehydrated tetrahydrofuran (35 ml) solution of N-(4-chloro-phenyl)-thioacetamide (3.3 g), 27 ml of n-butyl-lithium (1.59 mol/l, n-hexane solution) was added dropwise at 0° C. under a nitrogen atmosphere. After stirring at 0° C. for 1 hour, the mixture was cooled to −78° C. A tetrahydrofuran (35 ml) solution of 5-bromo-2-methyl-2-pentene (2.9 g) was added dropwise thereto. After raising the temperature to room temperature and further stirring for 30 minutes, an aqueous saturated ammonium chloride solution was added and then the reaction mixture was extracted with ethyl acetate. The organic layer was washed with saturated saline solution, dried over anhydrous magnesium sulfate, filtered and then concentrated under reduced pressure. The residue was purified by silica gel column chromatography to obtain 2.0 g of the target compound.

$^1$H-NMR of the obtained compound is shown below.
$^1$H-NMR (CDCl$_3$) δ ppm:
1.61 (s, 3H), 1.71 (s, 3H), 1.87 (m, 2H), 2.10 (m, 2H), 2.79 (t, 2H), 5.15 (m, 1H), 7.35 (d, 2H), 7.61 (d, 2H), 8.63 (brs, 1H)

(II) Synthesis of (4-chloro-phenyl)-[6-isopropylidene-tetrahydro-thiopyran-2-ylidene]-amine (Compound Represented by Formula (d')

In a tetrahydrofuran (40 ml) solution of 6-methyl-5-heptenethioic acid (4-chloro-phenyl)-amide (2.0 g), a tetrahydrofuran (15 ml) solution of iodine (2.3 g) was added dropwise at 0° C. The temperature was raised to room temperature, followed by stirring overnight. After cooling to 0° C., a tetrahydrofuran (5 ml) solution of diazabicycloundecene (2.9 g) was added dropwise. After raising the temperature to room temperature and further stirring for 1 hour, water was added and the reaction mixture was extracted with ethyl acetate. The organic layer was washed with a saturated saline solution, dried over anhydrous magnesium sulfate, filtered and then concentrated under reduced pressure. The residue was purified by silica gel column chromatography to obtain 1.1 g of the target compound.

$^1$H-NMR of the obtained compound is shown below.
$^1$H-NMR (CDCl$_3$) δ ppm:
1.70 (s, 3H), 1.74 (s, 3H), 1.95 (m, 2H), 2.62 (t, 2H), 2.72 (t, 2H), 6.81 (d, 2H), 7.27 (d, 2H)

(III) Synthesis of 2-(4-chloro-phenylamino)-6-isopropylidene-5,6-dihydro-4H-thiopyran-3-carbaldehyde (Compound Represented by Formula (e'))

In a dehydrated tetrahydrofuran (20 ml) solution of (4-chloro-phenyl)-[6-isopropylidene-tetrahydro-thiopyran-2-ylidene]-amine (1.1 g), 3.6 ml of lithium diisopropylamide (1.5 mol/l, tetrahydrofuran/cyclohexane solution) was added dropwise at −78° C. under a nitrogen atmosphere. After stirring at −78° C. for 30 minutes, a tetrahydrofuran (2 ml) solution of ethyl formate (0.39 g) was added dropwise. After raising the temperature to room temperature and further stirring for 1 hour, an aqueous saturated ammonium chloride solution was added and the reaction mixture was extracted with ethyl acetate. The organic layer was washed with a saturated saline solution, dried over anhydrous magnesium sulfate, filtered and then concentrated under reduced pressure. The residue was purified by silica gel column chromatography to obtain 0.45 g of the target compound.

$^1$H-NMR of the obtained compound is shown below.
$^1$H-NMR (CDCl$_3$) δ ppm:
1.76 (s, 3H), 1.78 (s, 3H), 2.50-2.60 (m, 4H), 7.22 (d, 2H), 7.31 (d, 2H), 8.89 (s, 1H), 12.93 (brs, 1H)

(IV) Synthesis of (4-chloro-phenyl)-{6-isopropylidene-3-[1-phenylsulfanyl-(E)-methylidene]-tetrahydro-thiopyran-(2Z)-ylidene}-amine (Compound Represented by Formula (g'))

In an N,N-dimethylformamide (10 ml) solution of 2-(4-chloro-phenylamino)-6-isopropylidene-5,6-dihydro-4H-thiopyran-3-carbaldehyde (0.44 g), triethylamine (0.23 g) and methanesulfonyl chloride (0.24 g) were added at 0° C. After raising the temperature to room temperature and further stirring for 1 hour, water was added and the reaction mixture was extracted with ethyl acetate. The organic layer was washed with water and a saturated saline solution, dried over anhydrous magnesium sulfate, filtered and then concentrated under reduced pressure to obtain a crude product of {3-[1-chloro-(E)-methylidene]-6-isopropylidene-tetrahydro-thiopyran-(2Z)-ylidene}-(4-chloro-phenyl)-amine.

In an N,N-dimethylformamide (10 ml) solution of thiophenol (0.17 g), an N,N-dimethylformamide (5 ml) solution of triethylamine (0.23 g) and the above crude product was added at 0° C. After raising the temperature to room temperature and further stirring for 30 minutes, water was added and the reaction mixture was extracted with ethyl acetate. The organic layer was washed with water and a saturated saline solution, dried over anhydrous magnesium sulfate, filtered and then concentrated under reduced pressure. The residue was purified by silica gel column chromatography to obtain 0.32 g of the target compound.

Physical properties and $^1$H-NMR of the obtained compound are shown below.
Melting point: 101-103° C.
$^1$H-NMR (CDCl$_3$) δ ppm:
1.69 (s, 3H), 1.77 (s, 3H), 2.58-2.71 (m, 4H), 6.80 (d, 2H), 7.19-7.31 (m, 5H), 7.47-7.50 (m, 3H)

[Chemical Formula 6]

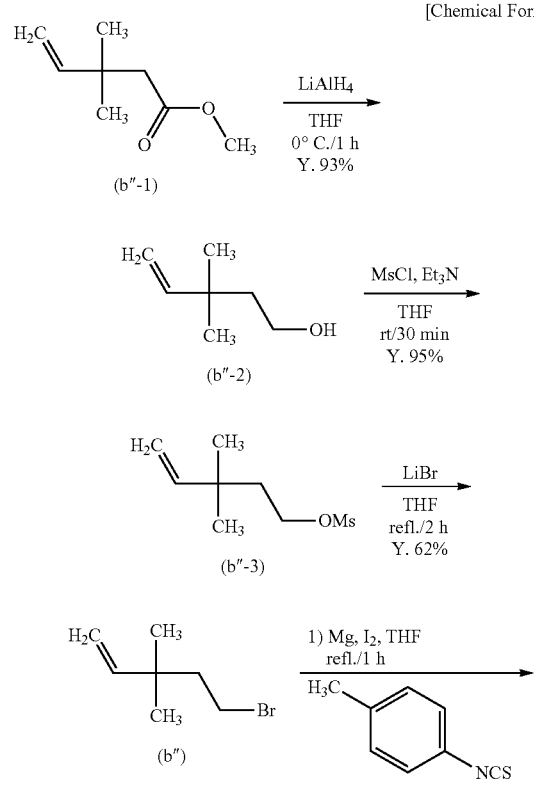

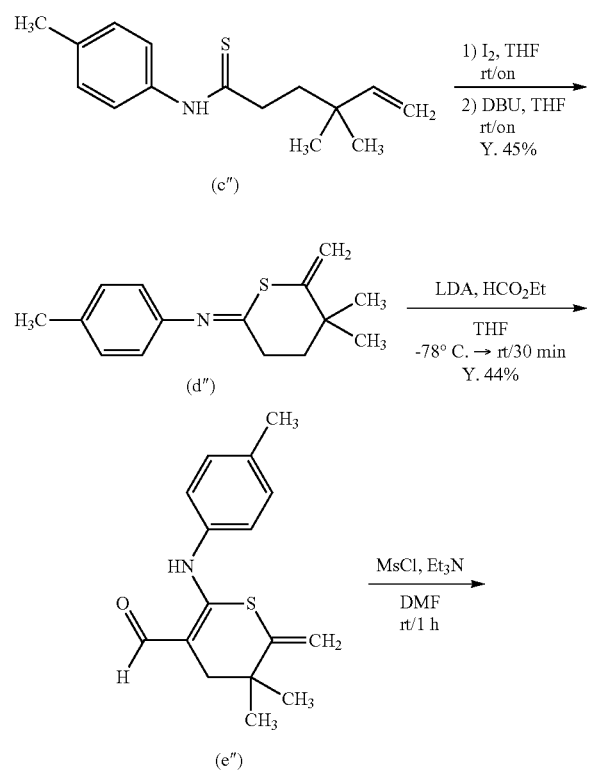

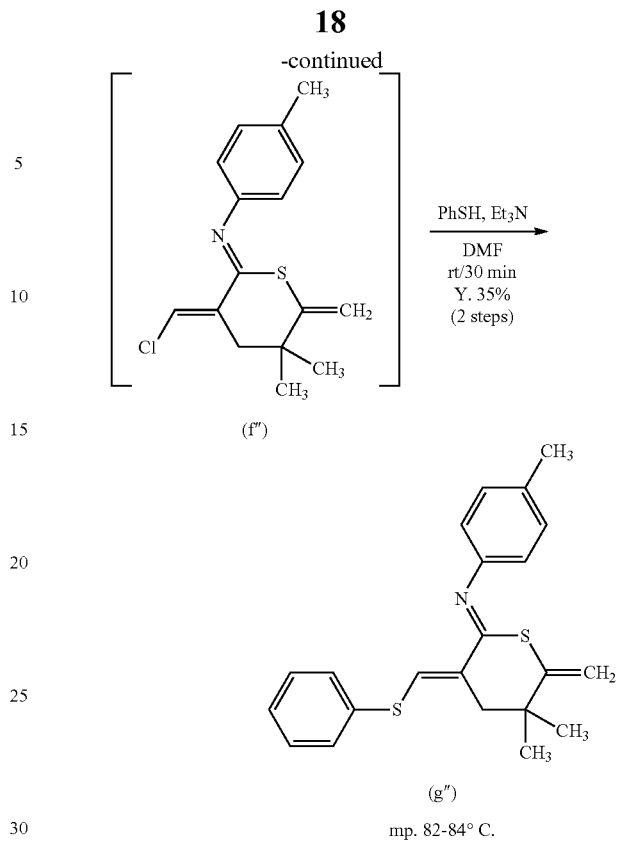

mp. 82-84° C.

Example 2

(I) Synthesis of 3,3-dimethyl-4-penten-1-ol (Compound Represented by Formula (b"-2))

Lithium aluminum hydride (1.3 g) was added to tetrahydrofuran (45 ml) at 0° C. To this suspension, a tetrahydrofuran (20 ml) solution of methyl 3,3-dimethyl-4-pentenoate (5.0 g) was added dropwise at 0° C. After stirring at 0° C. for 1 hour, an aqueous saturated sodium sulfate solution was added dropwise. After raising the temperature to room temperature, the precipitate was filtered and then dried over anhydrous magnesium sulfate. The precipitate was filtered and then concentrated under reduced pressure to obtain 3.6 g of the target compound.

$^1$H-NMR of the obtained compound is shown below.
$^1$H-NMR (CDCl$_3$) δ ppm:
1.04 (s, 6H), 1.62 (t, 2H), 3.65 (t, 2H), 4.92-4.99 (m, 2H), 5.80-5.90 (m, 1H)

(II) Synthesis of methanesulfonic acid 3,3-dimethyl-4-pentenyl ester (Compound Represented by Formula (b"-3))

In a tetrahydrofuran (30 ml) solution of 3,3-dimethyl-4-penten-1-ol (3.6 g), triethylamine (4.1 g) and methanesulfonyl chloride (4.3 g) were added at 0° C., followed by raising the temperature to room temperature and further stirring for 30 minutes. Water was added thereto and the reaction mixture was extracted with ethyl acetate. The organic layer was washed with saturated saline solution, dried over anhydrous magnesium sulfate, filtered and then concentrated under reduced pressure to obtain a crude product (5.7 g) of methanesulfonic acid 3,3-dimethyl-4-pentenyl ester. This crude product was subjected to a subsequent reaction without being purified.

(III) Synthesis of 5-bromo-3,3-dimethyl-1-pentene (Compound Represented by Formula (b''))

In a tetrahydrofuran (120 ml) solution of a crude product (5.7 g) of methanesulfonic acid 3,3-dimethyl-4-pentenyl ester, lithium bromide (7.7 g) was added at room temperature. The temperature was raised, followed by stirring under reflux for 2 hours. After cooling to room temperature, water was added and the reaction mixture was extracted with ethyl acetate. The organic layer was washed with saturated saline solution, dried over anhydrous magnesium sulfate, filtered and then concentrated under reduced pressure. The residue was purified by silica gel column chromatography to obtain 3.3 g of the target compound.

$^1$H-NMR of the obtained compound is shown below.
$^1$H-NMR (CDCl$_3$) δ ppm:
1.06 (s, 6H), 1.92 (t, 2H), 3.30 (t, 2H), 4.91-5.00 (m, 2H), 5.69-5.79 (m, 1H)

(IV) Synthesis of 4,4-dimethyl-5-hexenethioic acid p-tolylamide (Compound Represented by Formula (c''))

Magnesium (0.45 g) and a catalytic amount of iodine were added to dehydrated tetrahydrofuran (30 ml), and then a tetrahydrofuran solution (30 ml) of 5-bromo-3,3-dimethyl-1-pentene (3.3 g) was added dropwise under reflux. After stirring under reflux for 1 hour and further cooling to room temperature, a tetrahydrofuran solution of (3,3-dimethyl-4-pentenyl)magnesium bromide was obtained.

In a dehydrated tetrahydrofuran (30 ml) solution of p-tolyl isothiocyanate (1.8 g), a tetrahydrofuran solution of the above (3,3-dimethyl-4-pentenyl)magnesium bromide was added dropwise at 0° C., followed by stirring at 0° C. for 30 minutes. After raising the temperature to room temperature and further stirring for 30 minutes, an aqueous saturated ammonium chloride solution was added and the reaction mixture was extracted with ethyl acetate. The organic layer was washed with saturated saline solution, dried over anhydrous magnesium sulfate, filtered and then concentrated under reduced pressure. The residue was purified by silica gel column chromatography to obtain 1.2 g of the target compound.

$^1$H-NMR of the obtained compound is shown below.
$^1$H-NMR (CDCl$_3$) δ ppm:
1.07 (s, 6H), 1.89 (m, 2H), 2.35 (s, 3H), 2.70 (m, 2H), 4.95-5.03 (m, 2H), 5.76-5.85 (m, 1H), 7.20 (d, 2H), 7.48 (d, 2H), 8.53 (brs, 1H)

(V) Synthesis of [5,5-dimethyl-6-methylene-tetrahydro-thiopyran-2-ylidene]-p-tolyl-amine (Compound Represented by Formula (d''))

In a tetrahydrofuran (25 ml) solution of 4,4-dimethyl-5-hexenethioic acid p-tolylamide (1.2 g), a tetrahydrofuran (10 ml) solution of iodine (1.5 g) was added dropwise at 0° C., followed by raising the temperature to room temperature and further stirring overnight. After cooling to 0° C., a tetrahydrofuran (3 ml) solution of DBU (1.8 g) was added dropwise. After raising the temperature to room temperature and further stirring overnight, water was added and the reaction mixture was extracted with ethyl acetate. The organic layer was washed with a saturated saline solution, dried over anhydrous magnesium sulfate, filtered and then concentrated under reduced pressure. The residue was purified by silica gel column chromatography to obtain 0.53 g of the target compound.

$^1$H-NMR of the obtained compound is shown below.
$^1$H-NMR (CDCl$_3$) δ ppm:
1.29 (s, 6H), 1.80 (m, 2H), 2.34 (s, 3H), 2.80 (m, 2H), 5.12 (s, 1H), 5.16 (s, 1H), 6.76 (d, 2H), 7.13 (d, 2H)

(VI) Synthesis of 5,5-dimethyl-6-methylene-2-p-tolylamino-5,6-dihydro-4H-thiopyran-3-carbaldehyde (Compound Represented by Formula (e''))

In a dehydrated tetrahydrofuran (15 ml) solution of [5,5-dimethyl-6-methylene-tetrahydro-thiopyran-2-ylidene]-p-tolyl-amine (0.53 g), 2.2 ml of lithium diisopropylamide (1.5 mol/l, tetrahydrofuran/cyclohexane solution) was added dropwise at –78° C. under a nitrogen atmosphere. After stirring at –78° C. for 30 minutes, a tetrahydrofuran (1 ml) solution of ethyl formate (0.24 g) was added dropwise. After raising the temperature to room temperature and further stirring for 1 hour, an aqueous saturated ammonium chloride solution was added and the reaction mixture was extracted with ethyl acetate. The organic layer was washed with a saturated saline solution, dried over anhydrous magnesium sulfate, filtered and then concentrated under reduced pressure. The residue was purified by silica gel column chromatography to obtain 0.26 g of the target compound.

$^1$H-NMR of the obtained compound is shown below.
$^1$H-NMR (CDCl$_3$) δ ppm:
1.23 (s, 6H), 2.34 (m, 5H), 5.04 (s, 1H), 5.15 (s, 1H), 7.12-7.21 (m, 4H), 8.83 (s, 1H), 12.87 (brs, 1H)

(VII) Synthesis of {5,5-dimethyl-6-methylene-3-[1-phenylsulfanyl-(E)-methylidene]-tetrahydro-thiopyran-(2Z)-ylidene}-p-tolyl-amine (Compound Represented by Formula (g''))

In an N,N-dimethylformamide (5 ml) solution of 5,5-dimethyl-6-methylene-2-p-tolylamino-5,6-dihydro-4H-thiopyran-3-carbaldehyde (0.26 g), triethylamine (0.14 g) and methanesulfonyl chloride (0.16 g) were added at 0° C. After raising the temperature to room temperature and further stirring for 1 hour, water was added thereto and the reaction mixture was extracted with ethyl acetate. The organic layer was washed with water and a saturated saline solution, dried over anhydrous magnesium sulfate, filtered and then concentrated under reduced pressure to obtain a crude product of {3-[1-chloro-(E)-methylidene]-5,5-dimethyl-6-methylene-tetrahydro-thiopyran-(2Z)-ylidene}-p-tolyl-amine.

In an N,N-dimethylformamide (5 ml) solution of thiophenol (0.11 g), an N,N-dimethylformamide (2 ml) solution of triethylamine (0.14 g) and the above crude product was added at 0° C. After raising the temperature to room temperature and further stirring for 30 minutes, water was added thereto and the reaction mixture was extracted with ethyl acetate. The organic layer was washed with water and a saturated saline solution, dried over anhydrous magnesium sulfate, filtered and then concentrated under reduced pressure. The residue was purified by silica gel column chromatography to obtain 0.12 g of the target compound 0.12 g.

Physical properties and $^1$H-NMR of the obtained compound are shown below.
Melting point: 82-84° C.
$^1$H-NMR (CDCl$_3$) δ ppm:
1.34 (s, 6H), 2.33 (s, 3H), 2.57 (s, 2H), 5.01 (s, 1H), 5.09 (s, 1H), 6.77 (d, 2H), 7.13 (d, 2H), 7.25-7.38 (m, 3H), 7.50 (d, 2H), 7.62 (s, 1H)

Examples of the 1-heterodiene derivative according to the present invention produced in the same manner as mentioned above are shown in Tables 1 to 18. In the following tables, 2-(CH$_2$)$_5$-2 and 2-C$_2$H$_4$OC$_2$H$_4$-2 respectively mean that a cyclohexane ring and a tetrahydropyran ring are attached to the 2-position as a spiro ring.

TABLE 1

| Compound number | Q | X | W | Y | S(O)$_l$ | R$_m$ | R$^1$ | R$^2$ | Others | Physical properties |
|---|---|---|---|---|---|---|---|---|---|---|
| 1-1 | Ph | S | H | 4-Cl—Ph | S | — | H | H | | m.p. 74-75° C. |
| 1-2 | Ph | S | H | 4-Cl—Ph | S | — | Me | Me | | m.p. 69-71° C. |
| 1-3 | Ph | S | H | 4-Cl—Ph | S | — | Me | Me | HBF$_4$ salt | m.p. 112-113° C. |
| 1-4 | iPr | S | H | 4-Me—Ph | S | Me | —(CH$_2$)$_5$— | | | |
| 1-5 | CF$_3$ | S | H | 4-MeO—Ph | S | Et | H | H | | |
| 1-6 | MeOCH$_2$ | S | H | 4-CF$_3$—Ph | S | CF$_3$ | H | H | | |
| 1-7 | Bn | S | H | 4-F—Ph | S | H$_2$C=CH | H | Me | | |
| 1-8 | CH$_2$=CHCH$_2$ | S | H | 4-NMe$_2$—Ph | S | HC≡C | H | Et | | |
| 1-9 | MeC≡C | S | H | 2-Br—Ph | S | cPr | H | iPr | | |
| 1-10 | cPn | S | H | 3-cPr—Ph | S | cHex | Me | Me | | |
| 1-11 | 4-Cl-cHex | S | H | 4-Et—Ph | S | Ph | Et | Et | | |
| 1-12 | Naphtalen-1-yl | S | H | 3,5-F$_2$—Ph | S | 4-Cl—Ph | H | cPr | | |
| 1-13 | 4-CF$_3$—Ph | S | H | cPr | S | Pyridin-2-yl | H | CF$_3$ | | |
| 1-14 | 6-Cl-Pyridin-2-yl | S | H | cPen | S | — | Me | Me | | |
| 1-15 | Pyridin-4-yl | S | H | cHex | S | — | Me | Me | | |
| 1-16 | 2-Me-Furan-3-yl | S | H | Furan-3-yl | S | — | H | H | | |
| 1-17 | Ph | S | H | Thiophen-2-yl | S | Me | H | H | | |
| 1-18 | Thiophen-2-yl | S | H | Pyridin-2-yl | S | Et | H | H | | |
| 1-19 | 4-Me-Pyrimidin-2-yl | S | H | Ph | S | CF$_3$ | H | H | | |
| 1-20 | Ph | O | H | 4-Me—Ph | S | H$_2$C=CH | H | H | HCl salt | |
| 1-21 | Ph | O | H | 4-MeO—Ph | SO | HC≡C | H | H | H$_2$SO$_4$ salt | |
| 1-22 | Ph | O | H | 4-CF$_3$—Ph | SO | cPr | H | H | HBr salt | |
| 1-23 | Ph | O | H | 4-F—Ph | SO | cHex | H | H | | |
| 1-24 | Ph | SO | H | 4-NMe$_2$—Ph | SO | Ph | H | H | | |
| 1-25 | Ph | SO | H | 4-Me—Ph | SO | 4-Cl—Ph | H | H | | |
| 1-26 | Ph | SO | H | 4-MeO—Ph | SO | Pyridin-2-yl | H | H | | |
| 1-27 | Ph | SO$_2$ | H | 4-CF$_3$—Ph | SO$_2$ | Me$_2$ | H | H | | |
| 1-28 | Ph | SO$_2$ | H | 4-F—Ph | SO$_2$ | —(CH$_2$)$_5$— | H | H | | |
| 1-29 | Ph | SO$_2$ | H | 4-NMe$_2$—Ph | SO$_2$ | Me | H | H | | |
| 1-30 | Ph | SO$_2$ | H | 2,4-Me$_2$—Ph | SO$_2$ | Et | H | H | | |

TABLE 2

| Compound number | Q | X | W | Y | S(O)$_l$ | R$_m$ | R$^1$ | R$^2$ | Others | Physical properties |
|---|---|---|---|---|---|---|---|---|---|---|
| 2-1 | Ph | S | H | 4-Cl—Ph | S | — | H | H | | 2.72 (s, 4H), 4.96 (s, 1H), 5.08 (s, 1H), 6.78 (d, 2H), 7.27-7.39 (m, 5H), 7.49 (d, 2H), 7.60 (s, 1H) |
| 2-2 | Ph | S | H | 4-Cl—Ph | S | — | Me | Me | | m.p. 101-103° C. |
| 2-3 | Ph | S | H | 4-Cl—Ph | S | — | Et | H | | 0.91-0.99 (m, 3H), 1.95-2.12 (m, 2H), 2.66-2.71 (m, 4H) 5.42 (t, 1H), 6.75-7.57 (m, 9H) |
| 2-4 | Ph | S | H | 4-Me—Ph | S | — | H | H | | 2.33 (s, 3H), 2.72 (s, 4H), 4.94 (s, 1H), 5.05 (s, 1H), 6.75 (d, 2H), 7.13 (d, 2H), 7.15-7.45 (m, 3H), 7.49 (d, 2H), 7.58 (s, 1H) |

TABLE 2-continued

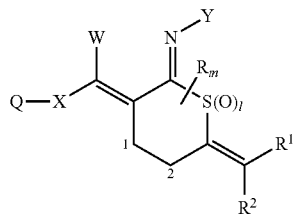

| Compound number | Q | X | W | Y | S(O)$_l$ | R$_m$ | R$^1$ | R$^2$ | Others | Physical properties |
|---|---|---|---|---|---|---|---|---|---|---|
| 2-5 | Ph | S | H | 4-CF$_3$—Ph | S | — | H | H | | 2.73 (s, 4H), 4.96 (s, 1H), 5.09 (s, 1H), 6.92 (d, 2H), 7.25-7.34 (m, 3H), 7.50 (d, 2H), 7.57 (d, 2H), 7.65 (s, 1H) |
| 2-6 | 4-F—Ph | S | H | 4-Me—Ph | S | — | H | H | | nD$^{22.0}$ 1.6478 |
| 2-7 | Pyridin-2-yl | S | H | 4-Me—Ph | S | — | H | H | | nD$^{22.1}$ 1.6818 |
| 2-8 | Ph | S | H | 4-MeO—Ph | S | — | H | H | | m.p. 101-103° C. |
| 2-9 | 4-F—Ph | S | H | 4-MeO—Ph | S | — | H | H | | m.p. 108-110° C. |
| 2-10 | Ph | S | H | cPn | S | — | H | H | | 1.54-1.97 (m, 8H), 2.62-2.70 (m, 4H), 3.89 (m, 1H), 5.06 (s, 1H), 5.10 (s, 1H), 7.29-7.48 (m, 6H) |
| 2-11 | Ph | S | H | 4-Me—Ph | S | 2,2-Me$_2$ | H | H | | m.p. 82-84° C. |
| 2-12 | Ph | S | H | 4-Cl—Ph | S | 2,2-Me$_2$ | H | H | | m.p. 107-109° C. |
| 2-13 | 4-F—Ph | S | H | 4-Cl—Ph | S | 2,2-Me$_2$ | H | H | | m.p. 110-112° C. |
| 2-14 | Ph | S | H | 4-Me—Ph | S | — | H | H | HBF$_4$ salt | m.p. 140-142° C. |

TABLE 3

| | | | | | | | | | |
|---|---|---|---|---|---|---|---|---|---|
| 2-15 | Ph | S | H | 4-Me—Ph | S | 2-Ph | H | H | 2.33 (s, 3H), 3.00-3.16 (m, 2H), 3.98-4.03 (m, 1H), 4.79 (s, 1H), 5.11 (s, 1H), 6.75 (d, 2H), 7.14 (d, 2H), 7.25-7.44 (m, 10H), 7.59 (s, 1H) |
| 2-16 | Ph | S | H | 4-MeO—Ph | S | 2,2-Me$_2$ | H | H | m.p. 71-73° C. |
| 2-17 | Ph | S | H | 4-Me—Ph | S | 2-(CH$_2$)$_5$-2 | H | H | m.p. 117-119° C. |
| 2-18 | 4-MeO—Ph | S | H | 4-Me—Ph | S | 2,2-Me$_2$ | H | H | m.p. 86-88° C. |
| 2-19 | 2-MeO—Ph | S | H | 4-Me—Ph | S | 2,2-Me$_2$ | H | H | m.p. 86-88° C. |
| 2-20 | 3-MeO—Ph | S | H | 4-Me—Ph | S | 2,2-Me$_2$ | H | H | 1.34 (s, 6H), 2.33 (s, 3H), 2.56 (s, 2H), 3.81 (s, 3H), 5.00 (s, 1H), 5.08 (s, 1H), 6.75-6.85 (m, 3H), 7.01-7.28 (m, 5H), 7.62 (s, 1H) |
| 2-21 | 4-AcNH—Ph | S | H | 4-Me—Ph | S | 2,2-Me$_2$ | H | H | m.p. 146-148° C. |
| 2-22 | 4-F—Ph | S | H | 4-MeO—Ph | S | — | Me | Me | 1.70 (s, 3H), 1.77 (s, 3H), 2.63-2.74 (m, 4H), 3.80 (s, 3H), 6.81-6.91 (m, 4H), 7.05 (t, 2H), 7.33 (s, 1H), 7.47 (d, 2H) |
| 2-23 | Ph | S | H | 4-MeO—Ph | S | — | Me | Me | m.p. 147-150° C. |
| 2-24 | 4-F—Ph | S | H | 4-Me—Ph | S | 2-(CH$_2$)$_5$-2 | H | H | m.p. 121-122° C. |
| 2-25 | Ph | S | H | 3-MeO—Ph | S | 2,2-Me$_2$ | H | H | 1.34 (s, 6H), 2.57 (s, 2H), 3.79 (s, 3H), 5.02 (s, 1H), 5.10 (s, 1H), 6.43-6.48 (m, 2H), 6.65 (dd, 1H), 7.20-7.37 (m, 5H), 7.49 (d, 2H), 7.63 (s, 1H) |
| 2-26 | Ph | S | H | 2-Cl-4-Me—Ph | S | 2,2-Me$_2$ | H | H | 1.34 (s, 6H), 2.34 (s, 3H), 2.56 (s, 2H), 5.03 (s, 1H), 5.11 (s, 1H), 6.68 (dd, 1H), 6.89 (d, 1H), 7.16 (d, 1H), 7.27-7.38 (m, 3H), 7.48 (d, 2H), 7.62 (s, 1H), |
| 2-27 | Ph | S | H | 2-MeO—Ph | S | 2,2-Me$_2$ | H | H | 1.35 (s, 6H), 2.57 (s, 2H), 3.80 (s, 3H), 4.98 (s, 1H), 5.09 (s, 1H), 6.78 (dd, 1H), 6.95 (m, 2H), 7.08 (dt, 1H), 7.26-7.36 (m, 3H), 7.49 (d, 2H), 7.69 (s, 1H) |

TABLE 4

| | | | | | | | | | |
|---|---|---|---|---|---|---|---|---|---|
| 2-28 | Ph | S | H | 3,4-MeO$_2$—Ph | S | 2,2-Me$_2$ | H | H | 1.35 (s, 6H), 2.58 (s, 2H), 3.86 (s, 3H), 3.87 (s, 3H), 5.04 (s, 1H), 5.11 (s, 1H), 6.44-6.50 (m, 2H), 6.83 (d, 1H), 7.28-7.38 (m, 3H), 7.49 (d, 2H), 7.61 (s, 1H) |

TABLE 4-continued

| | | | | | | | | | |
|---|---|---|---|---|---|---|---|---|---|
| 2-29 | Ph | S | H | 3-Cl—Ph | S | 2,2-Me$_2$ | H | H | 1.34 (s, 6H), 2.57 (s, 2H), 5.03 (s, 1H), 5.12 (s, 1H), 6.74 (dd, 1H), 6.87 (s, 1H), 7.07 (dd, 1H), 7.24-7.38 (m, 4H), 7.48 (d, 2H), 7.65 (s, 1H) |
| 2-30 | Ph | S | H | 2,4-MeO$_2$—Ph | S | 2,2-Me$_2$ | H | H | 1.34 (s, 6H), 2.57 (s, 2H), 3.78 (s, 3H), 3.82 (s, 3H), 4.99 (s, 1H), 5.07 (s, 1H), 6.44-6.49 (m, 2H), 6.72 (d, 1H), 7.27-7.36 (m, 3H), 7.49 (d, 2H), 7.65 (s, 1H) |
| 2-31 | Ph | S | H | 2,6-F$_2$—Ph | S | 2,2-Me$_2$ | H | H | 1.35 (s, 6H), 2.58 (s, 2H), 5.01 (s, 1H), 5.13 (s, 1H), 6.87-7.03 (m, 3H), 7.28-7.38 (m, 3H), 7.49 (d, 2H), 7.82 (s, 1H) |
| 2-32 | Ph | S | H | 3,5-Cl$_2$—Ph | S | 2,2-Me$_2$ | H | H | 1.34 (s, 6H), 2.55 (s, 2H), 5.05 (s, 1H), 5.14 (s, 1H) 6.76 (s, 2H), 7.06 (s, 1H), 7.26-7.39 (m, 3H), 7.48 (d, 2H), 7.65 (s, 1H) |
| 2-33 | Ph | S | H | 2-F-4-MeO—Ph | S | 2,2-Me$_2$ | H | H | 1.34 (s, 6H), 2.57 (s, 2H), 3.78 (s, 3H), 5.02 (s, 1H), 5.11 (s, 1H), 6.64-6.70 (m, 2H), 6.82 (t, 1H), 7.26-7.38 (m, 3H), 7.49 (d, 2H), 7.69 (s, 1H) |
| 2-34 | Ph | S | H | 4-MeO-3-Me—Ph | S | 2,2-Me$_2$ | H | H | 1.34 (s, 6H), 2.23 (s, 3H), 2.57 (s, 2H), 3.81 (s, 3H), 5.01 (s, 1H), 5.09 (s, 1H), 6.66-6.83 (m, 3H), 7.27-7.37 (m, 3H), 7.49 (d, 1H), 7.59 (s, 1H) |
| 2-35 | Ph | S | H | 3,4-Cl$_2$—Ph | S | 2,2-Me$_2$ | H | H | 1.34 (s, 6H), 2.56 (s, 2H), 5.03 (s, 1H), 5.13 (s, 1H), 6.71 (dd, 1H), 6.98 (s, 1H), 7.27-7.38 (m, 4H), 7.49 (d, 2H), 7.65 (s, 1H) |

TABLE 5

| | | | | | | | | | |
|---|---|---|---|---|---|---|---|---|---|
| 2-36 | Ph | S | H | 3-CF$_3$—Ph | S | 2,2-Me$_2$ | H | H | 1.35 (s, 6H), 2.58 (s, 2H), 5.02 (s, 1H), 5.13 (s, 1H), 7.04 (d, 1H), 7.13 (s, 1H), 7.27-7.45 (m, 5H), 7.49 (d, 1H), 7.72 (s, 1H) |
| 2-37 | Ph | S | H | 2,3-Cl$_2$—Ph | S | 2,2-Me$_2$ | H | H | 1.35 (s, 6H), 2.58 (s, 2H), 5.00 (s, 1H), 5.12 (s, 1H), 6.77 (dd, 1H), 7.11-7.39 (m, 5H), 7.49 (d, 2H), 7.80 (s, 1H) |
| 2-38 | Ph | S | H | 3,5-MeO—Ph | S | 2,2-Me$_2$ | H | H | 1.34 (s, 6H), 2.57 (s, 2H), 3.77 (s, 3H), 5.03 (s, 1H), 5.10 (s, 1H), 6.05 (s, 2H), 6.23 (s, 1H), 7.26-7.38 (m, 3H), 7.49 (d, 2H), 7.62 (s, 1H) |
| 2-39 | Ph | S | H | 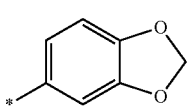 [SMILES: *c1ccc2c(c1)OCO2] | S | 2,2-Me$_2$ | H | H | 1.34 (s, 6H), 2.56 (s, 2H), 5.04 (s, 1H), 5.11 (s, 1H), 5.95 (s, 2H), 6.33 (d, 1H), 6.45 (s, 1H), 6.77 (d, 1H), 7.25-7.37 (m, 3H), 7.49 (d, 2H), 7.59 (s, 1H) |
| 2-40 | Ph | S | H | 4-MeO-2-Me—Ph | S | 2,2-Me$_2$ | H | H | 1.34 (s, 6H), 2.10 (s, 3H), 2.58 (s, 2H), 3.80 (s, 3H), 4.99 (s, 1H), 5.08 (s, 1H), 6.65-6.76 (m, 3H), 7.25-7.38 (m, 3H), 7.49 (d, 2H), 7.68 (s, 1H) |
| 2-41 | 4-F—Ph | S | H | 4-MeO-2-Me—Ph | S | 2,2-Me$_2$ | H | H | 1.34 (s, 6H), 2.08 (s, 3H), 2.55 (s, 2H), 3.80 (s, 3H), 4.99 (s, 1H), 5.08 (s, 1H), 6.65-6.76 (m, 3H), 7.05 (t, 2H), 7.46 (dd, 2H), 7.60 (s, 1H) |
| 2-42 | 4-MeO—Ph | S | H | 4-MeO-2-Me—Ph | S | 2,2-Me$_2$ | H | H | 1.34 (s, 6H), 2.08 (s, 3H), 2.55 (s, 2H), 3.78 (s, 3H), 3.80 (s, 3H), 4.98 (s, 1H), 5.07 (s, 1H), 6.63-6.75 (m, 3H), 6.86 (d, 2H), 7.43 (d, 2H), 7.57 (s, 1H) |
| 2-43 | Pyrimidin-2-yl | S | H | 4-MeO—Ph | S | — | Me | Me | m.p. 129-131° C. |
| 2-44 | Ph | S | H | 2,5-Cl$_2$—Ph | S | 2,2-Me$_2$ | H | H | 1.35 (s, 6H), 2.57 (s, 2H), 5.02 (s, 1H), 5.13 (s, 1H), 6.87 (s, 1H), 7.00 (d, 1H), 7.19-7.51 (m, 6H), 7.78 (s, 1H) |

TABLE 6

| | | | | | | | | | |
|---|---|---|---|---|---|---|---|---|---|
| 2-45 | Ph | S | H | 2,5-MeO$_2$—Ph | S | 2,2-Me$_2$ | H | H | 1.34 (s, 6H), 2.57 (s, 2H), 3.78 (s, 6H), 4.99 (s, 1H), 5.08 (s, 1H), 6.40 (d, 1H), 6.60 (dd, 1H), 6.83 (d, 1H), 7.25-7.36 (m, 3H), 7.48 (d, 2H), 7.69 (s, 1H) |

TABLE 6-continued

| | | | | | | | | | |
|---|---|---|---|---|---|---|---|---|---|
| 2-46 | 4-F—Ph | S | H | 4-MeO—Ph | S | 2,2-Me$_2$ | H | H | 1.34 (s, 6H), 2.55 (s, 2H), 3.80 (s, 3H), 5.02 (s, 1H), 5.10 (s, 1H), 6.81-6.89 (m, 4H), 7.02 (t, 2H), 7.45-7.48 (m, 2H), 7.49 (s, 1H) |
| 2-47 | Pyrimidin-2-yl | S | H | 4-MeO—Ph | S | 2,2-Me$_2$ | H | H | 1.33 (s, 6H), 2.59 (s, 2H), 3.82 (s, 3H), 5.01 (s, 1H), 5.08 (s, 1H), 6.91 (s, 4H), 7.06 (t, 1H), 8.43 (s, 1H), 8.59 (d, 2H) |
| 2-48 | 4-F—Ph | S | H | 4-Me—Ph | S | 2,2-Me$_2$ | H | H | m.p. 79-62° C. |
| 2-49 | 2-MeO—Ph | S | H | 4-MeO—Ph | S | 2,2-Me$_2$ | H | H | m.p. 108-111° C. |
| 2-50 | Pyridin-2-yl | S | H | 4-MeO—Ph | S | 2,2-Me$_2$ | H | H | m.p. 137-138° C. |
| 2-51 | Thiophen-2-yl | S | H | 4-MeO—Ph | S | 2,2-Me$_2$ | H | H | m.p. 87-89° C. |
| 2-52 | Ph | S | H | Thiophen-3-yl | S | — | H | H | m.p. 75-77° C. |
| 2-53 | Ph | S | H | Ph | S | 2,2-Me$_2$ | H | H | m.p. 91-94° C. |
| 2-54 | 4-F—Ph | S | H | Ph | S | 2,2-Me$_2$ | H | H | 1.34 (s, 6H), 2.56 (s, 2H), 5.00 (s, 1H), 5.10 (s, 1H), 6.85 (d, 2H), 6.98-7.13 (m, 3H), 7.30 (t, 2H), 7.42-7.53 (m, 3H) |
| 2-55 | Ph | O | H | 4-MeO—Ph | S | 2,2-Me$_2$ | H | H | 1.32 (s, 6H), 2.63 (s, 2H), 3.80 (s, 3H), 5.03 (s, 1H), 5.09 (s, 1H), 6.87 (s, 4H), 7.09-7.14 (m, 3H), 7.36 (t, 2H), 7.72 (s, 1H). |
| 2-56 | Ph | S | H | 4-Me—Ph | S | 2-C$_2$H$_4$CC$_2$H$_4$-2 | H | H | m.p. 134-136° C. |
| 2-57 | 4-F—Ph | S | H | 4-Me—Ph | S | 2-C$_2$H$_4$CC$_2$H$_4$-2 | H | H | m.p. 124-126° C. |
| 2-58 | cPn | S | H | 4-MeO—Ph | S | 2,2-Me$_2$ | H | H | 1.28 (s, 6H), 1.59-1.64 (m, 8H), 2.43 (s, 2H), 3.48 (m, 1H), 3.80 (s, 3H), 4.98 (s, 1H), 5.05 (s, 1H), 6.82-6.91 (m, 4H), 7.52 (s, 1H) |

TABLE 7

| | | | | | | | | | |
|---|---|---|---|---|---|---|---|---|---|
| 2-59 | Ph | S | H | 2-MeO-4-Me—Ph | S | 2,2-Me$_2$ | H | H | 1.34 (s, 6H), 2.35 (s, 3H), 2.57 (s, 2H), 3.78 (s, 3H), 4.98 (s, 1H), 5.06 (s, 1H), 6.66-6.80 (m, 3H), 7.25-7.36 (m, 3H), 7.48 (d, 2H), 7.66 (s, 1H) |
| 2-60 | 5-Me-1,3,4-Thiadiazol-2-yl | S | H | 4-MeO—Ph | S | 2,2-Me$_2$ | H | H | m.p. 112-114° C. |
| 2-61 | Ph | S | H | 4-IPrO—Ph | S | 2,2-Me$_2$ | H | H | 1.31-1.34 (m, 12H), 2.57 (s, 2H), 4.50 (m, 1H), 5.02 (s, 1H), 5.10 (s, 1H), 6.80-6.88 (m, 4H), 7.26-7.37 (m, 3H), 7.48 (d, 2H), 7.60 (s, 1H) |
| 2-62 | Ph | S | H | 2,6-Me$_2$—Ph | S | 2,2-Me$_2$ | H | H | 1.34 (s, 6H), 2.09 (s, 6H), 2.58 (s, 2H), 4.95 (s, 1H), 5.06 (s, 1H), 6.90-7.51 (m, 8H), 7.80 (s, 1H) |
| 2-63 | Ph | S | H | 2,4,6-Me$_3$—Ph | S | 2,2-Me$_2$ | H | H | 1.33 (s, 6H), 2.05 (s, 6H), 2.26 (s, 3H), 2.58 (s, 2H), 4.96 (s, 1H), 5.06 (s, 1H), 6.84 (s, 2H), 7.27-7.38 (m, 3H), 7.47 (d, 2H), 7.77 (s, 1H) |
| 2-64 | Ph | S | H | 2,4-Me$_2$—Ph | S | 2,2-Me$_2$ | H | H | 1.34 (s, 6H), 2.09 (s, 3H), 2.30 (s, 3H), 2.58 (s, 2H) 4.98 (s, 1H), 5.07 (s, 1H), 6.63 (d, 1H), 6.95-7.00 (m, 2H), 7.27-7.38 (m, 3H), 7.48 (m, 2H), 7.69 (s, 1H) |
| 2-65 | Ph | S | H | 2,6-F$_2$-4-MeO—Ph | S | 2,2-Me$_2$ | H | H | m.p. 121-123° C. |
| 2-66 | Thiophene-2-yl | S | H | 2,4,6-Me$_3$—Ph | S | 2,2-Me$_2$ | H | H | 1.34 (s, 6H), 2.02 (s, 6H), 2.25 (s, 3H), 2.54 (s, 2H), 4.94 (s, 1H), 5.05 (s, 1H), 6.83 (s, 2H), 7.01 (t, 1H), 7.23 (d, 1H), 7.40 (d, 1H), 7.55 (s, 1H) |
| 2-67 | Ph | S | H | 4-MeO-2,6-Me$_2$—Ph | S | 2,2-Me$_2$ | H | H | 1.34 (s, 6H), 2.06 (s, 6H), 2.58 (s, 2H), 3.77 (s, 3H), 4.96 (s, 1H), 5.06 (s, 1H), 6.60 (s, 2H), 7.26-7.38 (m, 3H), 7.47 (d, 2H), 7.77 (s, 1H) |

TABLE 8

| | | | | | | | | | |
|---|---|---|---|---|---|---|---|---|---|
| 2-68 | Ph | S | H | 4-Me—Ph | S | 2-Et | H | H | 0.97 (t, 3H), 1.58 (m, 1H), 1.71 (m, 1H), 2.32 (s, 3H), 2.65 (m, 1H), 2.73 (m, 2H), 4.98 (s, 1H), 5.06 (s, 1H), 6.76 (d, 2H), |

TABLE 8-continued

| | | | | | | | | | |
|---|---|---|---|---|---|---|---|---|---|
| 2-69 | 4,5-Me$_2$-Thiazol-2-yl | S | H | 4-MeO—Ph | S | 2,2-Me$_2$ | H | H | 7.15 (d, 2H), 7.28-7.37 (m, 3H), 7.49 (d, 2H), 7.62 (s, 1H), 1.26 (s, 6H), 2.32 (s, 6H), 2.59 (s, 2H), 4.99 (s, 1H), 5.07 (s, 1H), 6.87-7.00 (m, 4H), 7.26 (s, 1H) |
| 2-70 | 4-CN—Ph | S | H | 4-MeO—Ph | S | 2,2-Me$_2$ | H | H | 1.33 (s, 6H), 2.60 (s, 2H), 3.81 (s, 3H), 5.05 (s, 1H), 5.12 (s, 1H), 6.84-6.92 (m, 4H), 7.50-7.63 (m, 5H) |
| 2-71 | Thiophen-2-yl | S | H | 4-Me—Ph | S | 2,2-Me$_2$ | H | H | m.p. 136-138° C. |
| 2-72 | 4-CN—Ph | S | H | 4-Me—Ph | S | 2,2-Me$_2$ | H | H | 1.33 (s, 6H), 2.35 (s, 3H), 2.60 (s, 2H), 5.04 (s, 1H), 5.11 (s, 1H), 6.80 (d, 2H), 7.16 (d, 2H), 7.52 (d, 2H), 7.59 (s, 1H), 7.61 (d, 2H) |
| 2-73 | Thiazol-2-yl | S | H | 4-Me—Ph | S | 2,2-Me$_2$ | H | H | m.p. 118-122° C. |
| 2-74 | tBu | S | H | 4-Me—Ph | S | 2,2-Me$_2$ | H | H | m.p. 116-117° C. |
| 2-75 | Ph | S | H | 4-Me—Ph | S | 2-nPr | H | H | 0.95 (t, 3H), 1.39 (q, 2H), 1.45-1.69 (m, 2H), 2.33 (s, 3H), 2.71 (m, 3H), 4.97 (s, 1H), 5.05 (s, 1H), 6.77 (d, 2H), 7.13 (d, 2H), 7.26-7.37 (m, 3H), 7.50 (d, 2H), 7.62 (s, 1H) |
| 2-76 | Ph | S | H | 4-Me—Ph | S | 2-Me | H | H | 1.30 (d, 3H), 2.32 (s, 3H), 2.50 (m, 1H), 2.74-2.87 (m, 2H), 4.99 (s, 1H), 5.08 (s, 1H), 6.77 (d, 2H), 7.12 (d, 2H), 7.26-7.37 (m, 3H), 7.49 (d, 2H), 7.59 (s, 1H) |
| 2-77 | Thiophen-2-yl | S | H | 4-Me—Ph | S | 2-Me | H | H | m.p. 65-68° C. |
| 2-78 | Thiophen-3-yl | S | H | 4-Me—Ph | S | 2,2-Me$_2$ | H | H | m.p. 98-100° C. |
| 2-79 | 5-Me-Thiophen-2-yl | S | H | 4-Me—Ph | S | 2,2-Me$_2$ | H | H | m.p. 102-104° C. |
| 2-80 | 5-MeO-Thiophen-2-yl | S | H | 4-Me—Ph | S | 2,2-Me$_2$ | H | H | m.p. 94-96° C. |
| 2-81 | Thiophen-3-yl | S | H | 4-MeO—Ph | S | 2,2-Me$_2$ | H | H | m.p. 84-86° C. |

TABLE 9

| | | | | | | | | | |
|---|---|---|---|---|---|---|---|---|---|
| 2-82 | 4-CHO—Ph | S | H | 4-MeO—Ph | S | 2,2-Me$_2$ | H | H | 1.34 (s, 6H), 2.62 (s, 2H), 3.81 (s, 3H), 5.06 (s, 1H), 5.12 (s, 1H), 6.89 (m, 4H), 7.58 (d, 2H), 7.66 (s, 1H), 7.84 (d, 2H), 9.97 (s, 1H) |
| 2-83 | 5-Me-Thiophen-2-yl | S | H | 4-MeO—Ph | S | 2,2-Me$_2$ | H | H | m.p. 65-68° C. |
| 2-84 | 3-F—Ph | S | H | 4-Me—Ph | S | 2,2-Me$_2$ | H | H | m.p. 80-82° C. |
| 2-85 | 2-F—Ph | S | H | 4-Me—Ph | S | 2,2-Me$_2$ | H | H | m.p. 87-90° C. |
| 2-86 | 4-Me—Ph | S | H | 4-Me—Ph | S | 2,2-Me$_2$ | H | H | m.p. 96-97° C. |
| 2-87 | 4-Cl—Ph | S | H | 4-Me—Ph | S | 2,2-Me$_2$ | H | H | m.p. 96-97° C. |
| 2-88 | Naphtalen-2-yl | S | H | 4-Me—Ph | S | 2,2-Me$_2$ | H | H | m.p. 120-122° C. |
| 2-89 | Naphtalen-1-yl | S | H | 4-Me—Ph | S | 2,2-Me$_2$ | H | H | m.p. 124-126° C. |
| 2-90 | 4-CF3—Ph | S | H | 4-Me—Ph | S | 2,2-Me$_2$ | H | H | nD22.4 1.6159 |
| 2-91 | 6-Cl-Pyridin-2-yl | S | H | 4-Me—Ph | S | 2,2-Me$_2$ | H | H | m.p. 102-104° C. |
| 2-92 | Pyridin-4-yl | S | H | 4-Me—Ph | S | 2,2-Me$_2$ | H | H | nD22.5 1.6594 |
| 2-93 | 2-Me-Furan-3-yl | S | H | 4-Me—Ph | S | 2,2-Me$_2$ | H | H | m.p. 69-71° C. |
| 2-94 | 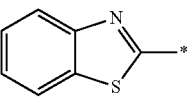 | S | H | 4-Me—Ph | S | 2,2-Me$_2$ | H | H | m.p. 80-82° C. |
| 2-95 | 5-CF3-Pyridin-2-yl | S | H | 4-MeO—Ph | S | 2,2-Me$_2$ | H | H | 1.33 (s, 6H), 2.59 (s, 2H), 3.83 (s, 3H), 5.06 (s, 1H), 5.12 (s, 1H), 6.93 (m, 4H), 7.43 (d, 1H), 7.78 (dd, 1H), 8.35 (s, 1H), 8.76 (s, 1H) |
| 2-96 | 2-CH2OH—Ph | S | H | 4-Me—Ph | S | 2,2-Me$_2$ | H | H | 1.36 (s, 6H), 2.33 (s, 3H), 3.22 (s, 2H), 4.82 (d, 2H), 5.02 (s, 1H), 5.10 (s, 1H), 6.76 (d, 2H), 7.13 (d, 2H), 7.34 (m, 2H), 7.46 (m, 2H), 7.56 (m, 1H) |
| 2-97 | 4-NMe2—Ph | S | H | 4-Me—Ph | S | 2,2-Me$_2$ | H | H | m.p. 134-136° C. |
| 2-98 | 4-CF$_3$-Pyrimidin-2-yl | S | H | 4-Me—Ph | S | 2,2-Me$_2$ | H | H | m.p. 105-108° C. |
| 2-99 | 3-CF$_3$—Ph | S | H | 4-Me—Ph | S | 2,2-Me$_2$ | H | H | nD22.2 1.5980 |
| 2-100 | 2-CF$_3$—Ph | S | H | 4-Me—Ph | S | 2,2-Me$_2$ | H | H | nD22.2 1.6016 |

TABLE 10

| | | | | | | | | | |
|---|---|---|---|---|---|---|---|---|---|
| 2-101 | 3-Br—Ph | S | H | 4-Me—Ph | S | 2,2-Me$_2$ | H | H | 1.33 (s, 6H), 2.34 (s, 3H), 2.56 (s, 2H), 5.03 (s, 1H), 5.10 (s, 1H), 6.91 (d, 2H), 7.14-7.24 (m, 3H), 7.40 (dd, 2H), 7.55 (s, 1H), 7.62 (s, 1H) |

TABLE 10-continued

| | | | | | | | | | |
|---|---|---|---|---|---|---|---|---|---|
| 2-102 | 2-Br—Ph | S | H | 4-Me—Ph | S | 2,2-Me$_2$ | H | H | 1.34 (s, 6H), 2.34 (s, 3H), 2.63 (s, 2H), 5.03 (s, 1H), 5.10 (s, 1H), 6.79 (d, 2H), 7.10-7.20 (m, 4H), 7.33 (m, 1H), 7.49-7.60 (m, 2H) |
| 2-103 | 5-SiMe$_3$-Thiophen-2-yl | S | H | 4-MeO—Ph | S | 2,2-Me$_2$ | H | H | m.p. 114-117° C. |
| 2-104 | 3-Me-Thiophen-2-yl | S | H | 4-Me—Ph | S | 2,2-Me$_2$ | H | H | m.p. 107-109° C. |
| 2-105 | 3-Ac—Ph | S | H | 4-Me—Ph | S | 2,2-Me$_2$ | H | H | 1.34 (s, 6H), 2.34 (s, 3H), 2.58 (s, 2H), 2.61 (s, 3H), 5.03 (s, 1H), 5.10 (s, 1H), 6.78 (d, 2H), 7.13 (d, 2H), 7.46 (m, 1H), 7.57 (s, 1H), 7.68 (d, 1H), 7.86 (d, 1H), 8.05 (d, 1H) |
| 2-106 | 3-CN—Ph | S | H | 4-Me—Ph | S | 2,2-Me$_2$ | H | H | m.p. 107-109° C. |
| 2-107 | 4-(3,5-F$_2$—Ph)-Pyrimidin-2-yl | S | H | 4-MeO—Ph | S | 2,2-Me$_2$ | H | H | m.p. 133-135° C. |
| 2-108 | 4-(Pyridin-2-yl)-Pyrimidin-2-yl | S | H | 4-MeO—Ph | S | 2,2-Me$_2$ | H | H | m.p. 160-162° C. |
| 2-109 | 3-PhO—Ph | S | H | 4-MeO—Ph | S | 2,2-Me$_2$ | H | H | m.p. 96-98° C. |
| 2-110 | 3-Me—Ph | S | H | 4-Me—Ph | S | 2,2-Me$_2$ | H | H | nD$^{22.5}$ 1.6376 |
| 2-111 | 2-Me—Ph | S | H | 4-Me—Ph | S | 2,2-Me$_2$ | H | H | m.p. 71-74° C. |
| 2-112 | Bn | S | H | 4-Me—Ph | S | 2,2-Me$_2$ | H | H | m.p. 111-112° C. |
| 2-113 | Quinolin-2-yl | S | H | 4-Me—Ph | S | 2,2-Me$_2$ | H | H | m.p. 112-113° C. |
| 2-114 | 2,6-F$_2$—Ph | S | H | 4-Me—Ph | S | 2,2-Me$_2$ | H | H | m.p. 103-105° C. |
| 2-115 | 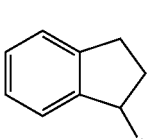 | S | H | 4-Me—Ph | S | 2,2-Me$_2$ | H | H | 1.29 (s, 6H), 2.28 (m, 1H), 2.34 (s, 3H), 2.45 (s, 1H), 2.66 (m, 1H), 2.89 (m, 1H), 3.12 (m, 1H), 4.72 (m, 1H), 4.98 (s, 1H), 5.05 (s, 1H), 6.79 (d, 2H), 7.15 (d, 2H), 7.19-7.25 (m, 3H), 7.39 (m, 1H), 7.61 (s, 1H) |
| 2-116 | 3-MeO-Thiophen-2-yl | S | H | 4-Me—Ph | S | 2,2-Me$_2$ | H | H | m.p. 93-95° C. |
| 2-117 | 5-Br-Thiophen-2-yl | S | H | 4-MeO—Ph | S | 2,2-Me$_2$ | H | H | m.p. 103-105° C. |
| 2-118 | Ph | S | H | 4-MeO—Ph | S | 1,2,2-Me$_3$ | H | H | m.p. 96-98° C. |
| 2-119 | 2,6-Me$_2$—Ph | S | H | 4-Me—Ph | S | 2,2-Me$_2$ | H | H | m.p. 122-124° C. |

TABLE 11

| | | | | | | | | | |
|---|---|---|---|---|---|---|---|---|---|
| 2-120 | 6-CF$_2$-Pyridin-2-yl | S | H | 4-Me—Ph | S | 2,2-Me$_2$ | H | H | 1.33 (s, 6H), 2.35 (s, 3H), 2.59 (s, 2H), 5.04 (s, 1H), 5.10 (s, 1H), 6.84 (d, 2H), 7.17 (d, 2H), 7.50 (m, 1H), 7.80 (m, 2H), 8.23 (s, 1H) |
| 2-121 | 4-Me-Pyrimidin-2-yl | S | H | 4-Me—Ph | S | 2,2-Me$_2$ | H | H | m.p. 128-131° C. |
| 2-122 | HC≡CCH$_2$ | S | H | 4-Me—Ph | S | 2,2-Me$_2$ | H | H | 1.29 (s, 6H), 2.30 (s, 1H), 2.32 (s, 3H), 2.45 (s, 2H), 3.57 (s, 2H), 4.99 (s, 1H), 5.06 (s, 1H), 6.78 (d, 2H), 7.15 (d, 2H), 7.51 (s, 1H) |
| 2-123 | 2,5-Me$_2$-Furan-3-yl | S | H | 4-Me—Ph | S | 2,2-Me$_2$ | H | H | 1.33 (s, 6H), 2.23 (s, 3H), 2.29 (s, 3H), 2.34 (s, 3H), 2.53 (s, 2H), 5.00 (s, 1H), 5.08 (s, 1H), 6.01 (s, 1H), 6.76 (d, 2H), 6.91 (d, 2H), 7.29 (s, 1H) |
| 2-124 | 2,4-F$_2$—Ph | S | H | 4-Me—Ph | S | 2,2-Me$_2$ | H | H | m.p. 82-84° C. |
| 2-125 | 4-tBu—Ph | S | H | 4-Me—Ph | S | 2,2-Me$_2$ | H | H | m.p. 107-108° C. |
| 2-126 | 4-CF$_3$-Pyridin-2-yl | S | H | 4-Me—Ph | S | 2,2-Me$_2$ | H | H | m.p. 106-108° C. |
| 2-127 | 4-Me-Pyrimidin-2-yl | S | H | 4-MeO—Ph | S | 2,2-Me$_2$ | H | H | m.p. 122-124° C. |
| 2-128 | 4-Me-Pyrimidin-2-yl | S | H | Ph | S | 2,2-Me$_2$ | H | H | m.p. 113-115° C. |
| 2-129 | Thiophen-2-yl | S | H | Ph | S | 2,2-Me$_2$ | H | H | m.p. 98-100° C. |
| 2-130 | Ph | S | H | 4-MeO—Ph | S | 2-Me-2-Me$_2$C═CHC$_2$H$_4$ | H | H | 1.31 (s, 3H), 1.48-1.77 (m, 8H), 2.00 (m, 2H), 2.46 (d, 1H), 2.70 (d, 1H9, 3.80 (s, 3H), 5.09 (m, 3H), 6.85 (m, 4H), 7.28-7.37 (m, 3H), 7.48 (d, 2H), 7.63 (s, 1H) |
| 2-131 | 3,6-Me$_2$-Pyrazin-2-yl | S | H | Ph | S | 2,2-Me$_2$ | H | H | m.p. 115-117° C. |
| 2-132 | 4-Me-Pyrimidin-2-yl | S | H | 3,4-Me$_2$—Ph | S | 2,2-Me$_2$ | H | H | m.p. 151-153° C. |
| 2-133 | 4-MeO-Pyrimidin-2-yl | S | H | 4-Me—Ph | S | 2,2-Me$_2$ | H | H | 1.33 (s, 6H), 2.35 (s, 3H), 2.65 (s, 2H), 4.00 (s, 3H), 5.02 (s, 1H), 5.09 (s, 1H), 6.48 (d, 1H), 7.15 (d, 1H), 8.28 (d, 1H), 8.50 (s, 1H) |
| 2-134 | 4-Cl-Pyrimidin-2-yl | S | H | 4-Me—Ph | S | 2,2-Me$_2$ | H | H | |
| 2-135 | 4,6-Me$_2$-Pyrimidin-2-yl | S | H | 4-Me—Ph | S | 2,2-Me$_2$ | H | H | m.p. 159-161° C. |
| 2-136 | 5-CF$_3$-Pyrimidin-2-yl | S | H | 4-Me—Ph | S | 2,2-Me$_2$ | H | H | |
| 2-137 | 1-Me-Tetrazol-5-yl | S | H | 4-Me—Ph | S | 2,2-Me$_2$ | H | H | m.p. 97-99° C. |
| 2-138 | 2-Me-Pyrimidin-4-yl | S | H | 4-Me—Ph | S | 2,2-Me$_2$ | H | H | |
| 2-139 | 2-CF$_3$-Pyrimidin-5-yl | S | H | 4-Me-Ph | S | 2,2-Me$_2$ | H | H | |

TABLE 12

| | | | | | | | | | |
|---|---|---|---|---|---|---|---|---|---|
| 2-140 | 2-Me-Thiophen-3-yl | S | H | 4-Me—Ph | S | 2,2-Me$_2$ | H | H | m.p. 83-85° C. |
| 2-141 | 4-Me-Thiophen-3-yl | S | H | 4-Me—Ph | S | 2,2-Me$_2$ | H | H | |
| 2-142 | 4-Br-Thiophen-3-yl | S | H | 4-Me—Ph | S | 2,2-Me$_2$ | H | H | |
| 2-143 | 4-Br-Thiophen-2-yl | S | H | 4-Me—Ph | S | 2,2-Me$_2$ | H | H | |
| 2-144 | Furan-2-yl | S | H | 4-Me—Ph | S | 2,2-Me$_2$ | H | H | |
| 2-145 | 5-Me-Furan-2-yl | S | H | 4-Me—Ph | S | 2,2-Me$_2$ | H | H | |
| 2-146 | 4-MeO-Furan-2-yl | S | H | 4-Me—Ph | S | 2,2-Me$_2$ | H | H | |
| 2-147 | Quinolin-8-yl | S | H | 4-Me—Ph | S | 2,2-Me$_2$ | H | H | |
| 2-148 | Ph | S | H | 3,4-Me$_2$—Ph | S | 2,2-Me$_2$ | H | H | m.p. 86-88° C. |
| 2-149 | Thiophen-2-yl | S | H | 3,4-Me$_2$—Ph | S | 2,2-Me$_2$ | H | H | m.p. 122-125° C. |
| 2-150 | 4-F—Ph | S | H | 3,4-Me$_2$—Ph | S | 2,2-Me$_2$ | H | H | m.p. 103-105° C. |
| 2-151 | 4-IPr—Ph | S | H | 4-Me—Ph | S | 2,2-Me$_2$ | H | H | m.p. 79-81° C. |
| 2-152 | Ph | S | H | 4-Me—Ph | S | 1,2,2-Me$_3$ | H | H | |
| 2-153 | Thiophen-2-yl | S | H | 4-Me—Ph | S | 1,2,2-Me$_3$ | H | H | |
| 2-154 | 4-Me-Pyrimidin-2-yl | S | H | 4-Me—Ph | S | 1,2,2-Me$_3$ | H | H | |
| 2-155 | Ph | S | H | 4-Me—Ph | S | 1,1-Me$_2$ | H | H | |
| 2-156 | Ph | S | H | 4-Me—Ph | S | 1,1,2,2-Me$_4$ | H | H | |
| 2-157 | Ph | S | H | 4-Me—Ph | S | 1-Et-2,2-Me$_2$ | H | H | |
| 2-158 | H$_2$C═CH | SO | H | Pyridin-2-yl | SO | 2-cPr | Me | Me | |
| 2-159 | HC≡CCH$_2$ | SO$_2$ | H | Thiophen-3-yl | SO$_2$ | 1-Ph | H | cHex | |
| 2-160 | 4-Me—Ph | O | H | Naphtalen-2-yl | SO$_2$ | 1,2-Me$_2$ | H | H | |

TABLE 13

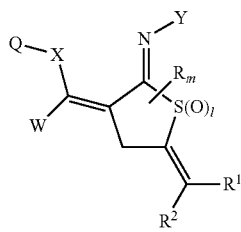

| Compound number | Q | X | W | Y | S(O)$_l$ | R$_m$ | R$^1$ | R$^2$ |
|---|---|---|---|---|---|---|---|---|
| 3-1 | Ph | S | H | 4-Cl—Ph | S | — | H | H |
| 3-2 | Ph | S | H | 4-Cl—Ph | S | — | Me | Me |
| 3-3 | Ph | S | H | 4-Cl—Ph | S | — | Me | Me |
| 3-4 | iPr | S | H | 4-Me—Ph | S | Me | —(CH$_2$)$_5$— | |
| 3-5 | CF$_3$ | S | H | 4-MeO—Ph | S | Et | H | H |
| 3-6 | MeOCH$_2$ | S | H | 4-CF$_3$—Ph | S | CF$_3$ | H | H |
| 3-7 | Bn | S | H | 4-F—Ph | S | H$_2$C═CH | H | Me |
| 3-8 | CH$_2$═CHCH$_2$ | S | H | 4-NMe$_2$—Ph | S | HC≡C | H | Et |
| 3-9 | MeC≡C | S | H | 2-Br—Ph | S | cPr | H | iPr |
| 3-10 | cPn | S | H | 3-cPr—Ph | S | cHex | Me | Me |
| 3-11 | 4-Cl-cHex | S | H | 4-Et—Ph | S | Ph | Et | Et |
| 3-12 | Naphtalen-1-yl | S | H | 3,5-F$_2$—Ph | S | 4-Cl—Ph | H | cPr |
| 3-13 | 4-CF$_3$—Ph | S | H | cPr | S | Pyridin-2-yl | H | CF$_3$ |
| 3-14 | 6-Cl-Pyridin-2-yl | S | H | cPen | S | — | Me | Me |
| 3-15 | Pyridin-4-yl | S | H | cHex | S | — | Me | Me |
| 3-16 | 2-Me-Furan-3-yl | S | H | Furan-3-yl | S | — | H | H |
| 3-17 | Ph | S | H | Thiophen-2-yl | S | Me | H | H |
| 3-18 | Thiophen-2-yl | S | H | Pyridin-2-yl | S | Et | H | H |
| 3-19 | 4-Me-Pyrimidin-2-yl | S | H | Ph | S | CF$_3$ | H | H |
| 3-20 | Ph | O | H | 4-Me—Ph | S | H$_2$C═CH | H | H |
| 3-21 | Ph | O | H | 4-MeO—Ph | SO | HC≡C | H | H |
| 3-22 | Ph | O | H | 4-CF$_3$—Ph | SO | cPr | H | H |
| 3-23 | Ph | O | H | 4-F—Ph | SO | cHex | H | H |
| 3-24 | Ph | SO | H | 4-NMe$_2$—Ph | SO | Ph | H | H |
| 3-25 | Ph | SO | H | 4-Me—Ph | SO | 4-Cl—Ph | H | H |
| 3-26 | Ph | SO | H | 4-MeO—Ph | SO | Pyridin-2-yl | H | H |
| 3-27 | Ph | SO$_2$ | H | 4-CF$_3$—Ph | SO$_2$ | Me$_2$ | H | H |
| 3-28 | Ph | SO$_2$ | H | 4-F—Ph | SO$_2$ | —(CH$_2$)$_5$— | H | H |
| 3-29 | Ph | SO$_2$ | H | 4-NMe$_2$—Ph | SO$_2$ | Me | H | H |
| 3-30 | Ph | SO$_2$ | H | 2,4-Me$_2$—Ph | SO$_2$ | Et | H | H |

TABLE 14

| Compound number | Q | X | W | Y | S(O)$_l$ | R$_m$ | R$^1$ | R$^2$ | Physical properties |
|---|---|---|---|---|---|---|---|---|---|
| 4-1 | Pyridin-2-yl | S | H | 4-Me—Ph | S | — | H | H | m.p. 123-124° C. |
| 4-2 | Pyridin-2-yl | S | H | 4-MeO—Ph | S | 2,2-Me$_2$ | H | H | m.p. 94-95° C. |
| 4-3 | Thiazol-2-yl | S | H | 4-Me—Ph | S | 2,2-Me$_2$ | H | H | m.p. 93-96° C. |
| 4-4 | Thiophen-2-yl | S | H | 4-MeO—Ph | S | 2,2-Me$_2$ | H | H | 1.26 (s, 6H), 2.47 (s, 2H), 3.82 (s, 3H), 5.00 (s, 1H), 5.07 (s, 1H), 6.58 (s, 1H), 6.90-7.03 (m, 4H), 7.18 (d, 1H), 7.37 (m, 2H) |
| 4-5 | Thiophen-2-yl | S | H | 4-MeO—Ph | SO | 2,2-Me$_2$ | H | H | 1.29 (s, 3H), 1.35 (s, 3H), 2.35 (d, 1H), 2.68 (d, 1H), 3.82 (s, 3H), 5.10 (s, 1H), 5.18 (s, 1H), 6.46 (s, 1H), 6.90-6.97 (m, 4H), 7.05 (dd, 1H), 7.47 (d, 1H), 7.56 (d, 1H) |
| 4-6 | benzothiazol-2-yl | S | H | 4-Me—Ph | S | 2,2-Me$_2$ | H | H | m.p. 142-144° C. |
| 4-7 | 4-CF$_3$-Pyridin-2-yl | S | H | 4-Me—Ph | S | 2,2-Me$_2$ | H | H | 1.28 (s, 6H), 2.37 (s, 3H), 2.67 (s, 2H), 4.99 (s, 1H), 5.07 (s, 1H), 6.90 (d, 1H), 7.20 (d, 2H), 7.27 (d, 1H), 7.49 (s, 1H), 7.89 (s, 1H), 8.68 (d, 1H) |
| 4-8 | Ph | S | H | 3,4-Me$_2$—Ph | S | 2,2-Me$_2$ | H | H | |
| 4-9 | Thiophen-2-yl | S | H | 3,4-Me$_2$—Ph | S | 2,2-Me$_2$ | H | H | |
| 4-10 | 4-F—Ph | S | H | 3,4-Me$_2$—Ph | S | 2,2-Me$_2$ | H | H | |

TABLE 15

| | | | | | | | | |
|---|---|---|---|---|---|---|---|---|
| 4-11 | 4-IPr—Ph | S | H | 4-Me—Ph | S | 2,2-Me$_2$ | H | H |
| 4-12 | Ph | S | H | 4-Me—Ph | S | 1,2,2-Me$_3$ | H | H |
| 4-13 | Thiophen-2-yl | S | H | 4-Me—Ph | S | 1,2,2-Me$_3$ | H | H |
| 4-14 | 4-Me-Pyrimidin-2-yl | S | H | 4-Me—Ph | S | 1,2,2-Me$_3$ | H | H |
| 4-15 | Ph | S | H | 4-Me—Ph | S | 1,1-Me$_2$ | H | H |
| 4-16 | Ph | S | H | 4-Me—Ph | S | 1,1,2,2-Me$_4$ | H | H |
| 4-17 | Ph | S | H | 4-Me—Ph | S | 1-Et-2,2-Me$_2$ | H | H |
| 4-18 | H$_2$C=CH | SO | H | Pyridin-2-yl | SO | 2-cPr | Me | Me |
| 4-19 | HC≡CCH$_2$ | SO$_2$ | H | Thiophen-3-yl | SO$_2$ | 1-Ph | H | cHex |
| 4-20 | 4-Me—Ph | O | H | Naphtalen-2-yl | SO$_2$ | 1,2-Me$_2$ | H | H |
| 4-21 | 4-Cl—cHex | S | H | 4-Et—Ph | S | 1-Ph | Et | Et |
| 4-22 | Naphtalen-1-yl | S | H | 3,5-F$_2$—Ph | S | 1,2-Ph$_2$ | H | cPr |
| 4-23 | 4-CF$_3$—Ph | S | H | cPr | S | 1,1,2,2-Me$_4$ | H | CF$_3$ |
| 4-24 | 6-Cl-Pyridin-2-yl | S | H | cPen | S | — | Me | Me |
| 4-25 | Pyridin-4-yl | S | H | cHex | S | — | Me | Me |
| 4-26 | 2-Me-Furan-3-yl | S | H | Furan-3-yl | S | — | H | H |
| 4-27 | Ph | S | H | Thiophen-2-yl | S | 1-Me | H | H |
| 4-28 | Thiophen-2-yl | S | H | Pyridin-2-yl | S | 2-Et | H | H |
| 4-29 | 4-Me-Pyrimidin-2-yl | S | H | Ph | S | 2-CF$_3$ | H | H |
| 4-30 | Ph | S | H | 4-MeO—Ph | S | — | Me | Et |

TABLE 16

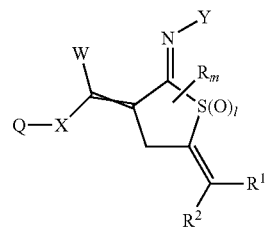

| Compound number | Q | X | W | Y | S(O)$_l$ | R$_m$ | R$^1$ | R$^2$ |
|---|---|---|---|---|---|---|---|---|
| 5-1 | Ph | S | H | 4-Cl—Ph | S | — | H | H |
| 5-2 | Ph | S | H | 4-Cl—Ph | S | — | Me | Me |
| 5-3 | Ph | S | H | 4-Cl—Ph | S | — | Me | Me |
| 5-4 | iPr | S | H | 4-Me—Ph | S | Me | —(CH$_2$)$_5$— | |
| 5-5 | CF$_3$ | S | H | 4-MeO—Ph | S | Et | H | H |
| 5-6 | MeOCH$_2$ | S | H | 4-CF$_3$—Ph | S | CF$_3$ | H | H |
| 5-7 | Bn | S | H | 4-F—Ph | S | H$_2$C=CH | H | Me |
| 5-8 | CH$_2$=CHCH$_2$ | S | H | 4-NMe$_2$—Ph | S | HC≡C | H | Et |
| 5-9 | MeC≡C | S | H | 2-Br—Ph | S | cPr | H | iPr |
| 5-10 | cPn | S | H | 3-cPr—Ph | S | cHex | Me | Me |
| 5-11 | 4-Cl-cHex | S | H | 4-Et—Ph | S | Ph | Et | Et |
| 5-12 | Naphtalen-1-yl | S | H | 3,5-F$_2$—Ph | S | 4-Cl—Ph | H | cPr |
| 5-13 | 4-CF$_3$—Ph | S | H | cPr | S | Pyridin-2-yl | H | CF$_3$ |
| 5-14 | 6-Cl-Pyridin-2-yl | S | H | cPen | S | — | Me | Me |
| 5-15 | Pyridin-4-yl | S | H | cHex | S | — | Me | Me |
| 5-16 | 2-Me-Furan-3-yl | S | H | Furan-3-yl | S | — | H | H |
| 5-17 | Ph | S | H | Thiophen-2-yl | S | Me | H | H |
| 5-18 | Thiophen-2-yl | S | H | Pyridin-2-yl | S | Et | H | H |
| 5-19 | 4-Me-Pyrimidin-2-yl | S | H | Ph | S | CF$_3$ | H | H |
| 5-20 | Ph | O | H | 4-Me—Ph | S | H$_2$C=CH | H | H |
| 5-21 | Ph | O | H | 4-MeO—Ph | SO | HC≡C | H | H |
| 5-22 | Ph | O | H | 4-CF$_3$—Ph | SO | cPr | H | H |
| 5-23 | Ph | O | H | 4-F—Ph | SO | cHex | H | H |
| 5-24 | Ph | SO | H | 4-NMe$_2$—Ph | SO | Ph | H | H |
| 5-25 | Ph | SO | H | 4-Me—Ph | SO | 4-Cl—Ph | H | H |
| 5-26 | Ph | SO | H | 4-MeO—Ph | SO | Pyridin-2-yl | H | H |
| 5-27 | Ph | SO$_2$ | H | 4-CF$_3$—Ph | SO$_2$ | Me$_2$ | H | H |
| 5-28 | Ph | SO$_2$ | H | 4-F—Ph | SO$_2$ | —(CH$_2$)$_5$— | H | H |
| 5-29 | Ph | SO$_2$ | H | 4-NMe$_2$—Ph | SO$_2$ | Me | H | H |
| 5-30 | Ph | SO$_2$ | H | 2,4-Me$_2$—Ph | SO$_2$ | Et | H | H |

TABLE 17

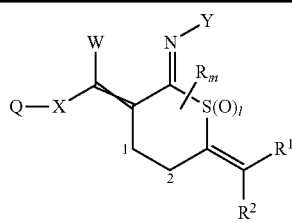

| Compound number | Q | X | W | Y | S(O)$_l$ | R$_m$ | R$^1$ | R$^2$ | Physical properties |
|---|---|---|---|---|---|---|---|---|---|
| 6-1 | Ph | S | H | 4-Me—Ph | S | — | Me | Me | nD$^{22.7}$ 1.6565 |
| 6-2 | 4-F—Ph | S | H | 4-Me—Ph | S | — | Me | Me | 1.67-1.77 (m, 6H), 2.33 (d, 3H), 2.67-2.71 (m, 4H), 6.60-7.50 (m, 9H) |
| 6-3 | 4-MeCN=CH—Ph | S | H | 4-MeO—Ph | S | 2,2-Me$_2$ | H | H | 1.31 (s, 3H), 1.34 (s, 3H), 2.54 (s, 1H), 2.58 (s, 1H), 3.80 (s, 1.5H), 3.82 (s, 1.5H), 3.87 (s, 1.5H), 3.88 (1.5H), 5.02 (s, 0.5H), 5.04 (s, 0.5H), 5.08 (s, 0.5H), 5.10 (s, 0.5H), 6.69 (s, 0.5H), 6.81-6.99 (m, 4H), 7.35 (m, 1H), 7.47-7.51 (m, 2H) |

TABLE 17-continued

| Compound number | Q | X | W | Y | S(O)$_l$ | R$_m$ | R$^1$ | R$^2$ | Physical properties |
|---|---|---|---|---|---|---|---|---|---|
| 6-4 | 4-NO$_2$—Ph | S | H | 4-Me—Ph | S | 2,2-Me$_2$ | H | H | 1.22 (s, 1.8H), 1.34 (s, 4.2H), 2.36 (s, 4.4H), 2.62 (s, 0.6H), 4.93 (s, 0.3H), 5.10 (s, 0.3H), 5.05 (s, 0.7H), 5.12 (s, 0.7H), 6.80-8.21 (m, 9H) |
| 6-5 | cHex | S | H | 4-Me—Ph | S | 2,2-Me$_2$ | H | H | nD$^{22.4}$ 1.6183 |
| 6-6 | Pyridin-3-yl | S | H | 4-Me—Ph | S | 2,2-Me$_2$ | H | H | m.p. 81-90° C. |
| 6-7 | 2,4-F$_2$—Ph | S | H | 4-Me—Ph | S | 2,2-Me$_2$ | H | H | 1.29 (s, 3H), 1.33 (s, 3H), 2.34 (s, 1.5H), 2.36 (s, 1.5H), 2.54 (s, 1H), 2.57 (s, 1H), 5.01 (s, 0.5H), 5.03 (s, 0.5H), 5.08 (s, 0.5H), 5.10 (s, 0.5H), 6.61 (s, 0.5H), 6.72 (m, 1H), 6.79 (d, 1H), 6.90 (d, 1H), 7.00 (m, 2H), 7.17 (m, 1H), 7.54 (s, 0.5H) |

TABLE 18

| Compound number | Q | X | W | Y | S(O)$_l$ | R$_m$ | R$^1$ | R$^2$ | Physical properties |
|---|---|---|---|---|---|---|---|---|---|
| 6-8 | Benzothiophen-2-yl | S | H | 4-Me—Ph | S | 2,2-Me$_2$ | H | H | 1.26 (s, 4H), 1.32 (s, 2H), 2.32 (s, 1H), 2.36 (s, 2H), 2.50 (s, 1.33H), 2.57 (s, 0.67H), 5.00 (s, 0.67H), 5.02 (s, 0.33H), 5.07 (s, 0.67H), 5.10 (s, 0.33H), 6.75 (m, 1.33H), 6.93 (d, 1.33H), 7.11-7.45 (m, 6.34H), 7.56 (s, 0.33H), 7.70-7.78 (m, 2H) |
| 6-9 | 3,6-Me$_2$-Pyrazin-2-yl | S | H | 4-Me—Ph | S | 2,2-Me$_2$ | H | H | 1.29 (s, 3H), 1.34 (s, 3H), 2.37 (m, 3H), 2.52 (m, 6H), 2.62 (s, 1H), 2.68 (s, 1H), 5.00 (s, 0.5H), 5.03 (s, 0.5H), 5.07 (s, 0.5H), 5.10 (s, 0.5H), 6.85 (d, 1H), 6.90 (d, 1H), 7.19 (m, 2H), 7.88 (s, 0.5H), 8.08 (s, 1H), 8.47 (s, 0.5H) |
| 6-10 | Me | SO | H | 4-F—Ph | SO | 2,2-Me$_2$ | H | H | |
| 6-11 | CF$_3$ | SO | H | 3,5-Me$_2$—Ph | SO | 2,2-Me$_2$ | H | H | |
| 6-12 | Bn | SO | H | 4-MeO—Ph | SO | 1,2,2-Me$_3$ | H | H | |
| 6-13 | cPr | SO | H | 2-F—Ph | SO | 1,2,2-Me$_3$ | H | H | |
| 6-14 | cHex | SO | H | 2-Br—Ph | SO | 1,2,2-Me$_3$ | H | H | |
| 6-15 | Ph | SO | H | 4-Me—Ph | SO | 1,1-Me$_2$ | H | H | |
| 6-16 | Ph | SO$_2$ | H | cPr | SO$_2$ | 1,1,2,2-Me$_4$ | H | H | |
| 6-17 | Ph | SO$_2$ | H | cBu | SO$_2$ | 1-Et-2,2-Me$_2$ | H | H | |
| 6-18 | Ph | SO$_2$ | H | cPen | SO$_2$ | 2-cPr | H | H | |
| 6-19 | Ph | SO$_2$ | H | cHex | SO$_2$ | 1-Ph | H | H | |
| 6-20 | Ph | SO$_2$ | H | Ph | SO$_2$ | 1,2-Me$_2$ | Me | Me | |
| 6-21 | Ph | SO$_2$ | H | Ph | SO$_2$ | 2,2-Me$_2$ | H | cHex | |
| 6-22 | Ph | SO$_2$ | H | Pyridin-2-yl | SO$_2$ | 1,2,2-Me$_3$ | H | H | |
| 6-23 | Ph | SO$_2$ | H | Pyrazin-2-yl | SO$_2$ | 1,2,2-Me$_3$ | H | H | |
| 6-24 | Ph | SO$_2$ | H | Furan-2-yl | SO$_2$ | 1,2,2-Me$_3$ | H | H | |
| 6-25 | Ph | SO$_2$ | H | 4-NO$_2$—Ph | SO$_2$ | 1,1-Me$_2$ | Me | Me | |
| 6-26 | Ph | O | H | cPr | SO$_2$ | 1,1,2,2-Me$_4$ | H | cHex | |
| 6-27 | Ph | O | H | cBu | SO$_2$ | 1-Et-2,2-Me$_2$ | H | H | |
| 6-28 | Ph | O | H | cPen | SO$_2$ | 2-cPr | H | H | |
| 6-29 | Ph | O | H | cHex | SO$_2$ | 1-Ph | H | H | |
| 6-30 | Ph | O | H | Ph | SO$_2$ | 1,2-Me$_2$ | H | H | |

Formulation Examples

Examples of the compositions of the present invention will be shown below, and additives and addition proportions are changeable over a wide range without being limited to these Examples. Parts in Formulation Examples show parts by weight.

Formulation Example 1

Wettable Powder

| | |
|---|---|
| Compound of the present invention | 40 parts |
| Diatomaceous earth | 53 parts |
| Higher alcohol sulfate ester | 4 parts |
| Alkylnaphthalene sulfonate salt | 3 parts |

The above components are mixed homogenously and ground finely to obtain a wettable powder with 40% of active ingredient.

Formulation Example 2

Emulsifiable Concentrate

| | |
|---|---|
| Compound of the present invention | 30 parts |
| Xylene | 33 parts |
| Dimethylformamide | 30 parts |
| Polyoxyethylene alkyl allyl ether | 7 parts |

The above components were mixed and dissolved to obtain an emulsifiable concentrate with 30% of active ingredient.

Formulation Example 3

Dust

| | |
|---|---|
| Compound of the present invention | 10 parts |
| Talc | 89 parts |
| Polyoxyethylene alkyl allyl ether | 1 part |

The above components are mixed homogenously and ground finely to obtain a dust with 10% of active ingredient.

Formulation Example 4

Granules

| | |
|---|---|
| Compound of the present invention | 5 parts |
| Clay | 73 parts |
| Bentonite | 20 parts |
| Sodium dioctylsulfosuccinate salt | 1 part |
| Sodium phosphate | 1 part |

The above components are mixed and ground well and, after adding water thereto and kneading together, granulated and dried to obtain granules with 5% of active ingredient.

Formulation Example 5

Suspension

| | |
|---|---|
| Compound of the present invention | 10 parts |
| Sodium lignin sulfonate | 4 parts |
| Sodium dodecylbenzene sulfonate | 1 part |
| Xanthan gum | 0.2 part |
| Water | 84.8 parts |

The above components were mixed and subjected to wet-grinding until the grain size of 1 μm or less was achieved to obtain a suspending agent with 10% of active ingredient.

Test Examples of the pest control agent thus obtained according to the present invention are shown below. In respective Test Examples, the insecticidal rate (%) was determined by the following calculation equation.

Insecticidal rate (%)=(number of dead pests/number of released pests)×100

Test Example 1

Confirmation and Efficacy Tests Against Rice Armyworm (Mythimna Separata)

The emulsifiable concentrate obtained according to Formulation of Formulation Example 2 was diluted with water so as to control the concentration of the compound to 125 ppm. Leaves of corn were immersed in this diluted solution for 30 seconds and then air-dried. The leaves were put in a petri dish on which a filter paper is laid, and then five second instar larvae of rice armyworm were inoculated. After covering the petri dish with a glass lid, the petri dish was placed in a temperature-controlled room at a temperature of 25° C. and a humidity of 65%. After 5 days, life and death were examined and the insecticidal rate was determined. The test was repeated twice.

In the present test, the following compounds showed the insecticidal rate of 100%.

Compound numbers 1-2, 1-3, 2-1, 2-2, 2-3, 2-4, 2-5, 2-6, 2-7, 2-8, 2-9, 2-11, 2-12, 2-13, 2-14, 2-15, 2-16, 2-17, 2-18, 2-19, 2-20, 2-21, 2-22, 2-24, 2-25, 2-26, 2-27, 2-29, 2-30, 2-31, 2-33, 2-34, 2-35, 2-36, 2-37, 2-39, 2-40, 2-41, 2-42, 2-43, 2-44, 2-46, 2-47, 2-48, 2-49, 2-50, 2-51, 2-52, 2-53, 2-54, 2-55, 2-56, 2-57, 2-58, 2-59, 2-62, 2-63, 2-64, 2-65, 2-66, 2-67, 2-68, 2-70, 2-71, 2-72, 2-73, 2-74, 2-75, 2-76, 2-77, 2-78, 2-79, 2-80, 2-81, 2-82, 2-83, 2-84, 2-85, 2-86, 2-87, 2-88, 2-89, 2-90, 2-91, 2-92, 2-93, 2-94, 2-95, 2-96, 2-97, 2-98, 2-99, 2-100, 2-101, 2-102, 2-103, 2-104, 2-105, 2-106, 2-110, 2-111, 2-112, 2-113, 2-114, 2-115, 2-116, 2-117, 2-118, 2-119, 2-121, 2-122, 2-123, 2-124, 2-126, 2-127, 2-128, 2-129, 2-130, 2-131, 2-132, 2-133, 2-148, 2-149, 2-150, 2-151, 4-1, 4-2, 4-4, 4-7, 6-1, 6-2, 6-3, 6-4, 6-5, 6-6, 6-7, 6-8, and 6-9.

Test Example 2

Confirmation and Efficacy Tests Against Cotton Aphid (*Aphis Gossypii*)

The emulsifiable concentrate obtained according to Formulation of Formulation Example 2 was diluted with water so as to control the concentration of the compound to 125 ppm. Adults of cotton aphids were inoculated to a cucumber plant (approximately 10 days after sprouting) sown in a 3 sun/size pot (9 cm). After 1 day, adult aphids were removed and the diluted solution was sprayed over the cucumber plant on which delivered nymphs are parasitic. The pot was placed in a temperature-controlled room at a temperature of 25° C. and a humidity of 65%. After 5 days, life and death were examined and the insecticidal rate was determined. The test was repeated twice.

In the present test, the following compounds showed the insecticidal rate of 100%.

Compound numbers 2-2, 2-3, 2-4, 2-6, 2-7, 2-8, 2-9, 2-11, 2-12, 2-13, 2-14, 2-15, 2-16, 2-17, 2-18, 2-19, 2-20, 2-22, 2-23, 2-25, 2-26, 2-29, 2-30, 2-31, 2-33, 2-34, 2-35, 2-36, 2-37, 2-39, 2-40, 2-41, 2-42, 2-46, 2-47, 2-48, 2-49, 2-50, 2-51, 2-52, 2-53, 2-54, 2-55, 2-56, 2-57, 2-58, 2-62, 2-63, 2-64, 2-65, 2-66, 2-67, 2-68, 2-70, 2-71, 2-72, 2-73, 2-75, 2-76, 2-77, 2-78, 2-79, 2-80, 2-81, 2-83, 2-84, 2-85, 2-86, 2-87, 2-89, 2-90, 2-91, 2-93, 2-94, 2-97, 2-98, 2-99, 2-100, 2-103, 2-110, 2-112, 2-117, 2-118, 2-121, 2-122, 2-124, 2-126, 2-127, 2-128, 2-129, 2-132, 2-148, 2-149, 2-150, 4-4, and 6-1.

Test Example 3

Confirmation and Efficacy Tests Against Sweetpotato Whitefly (*Bemisia Tabaci*)

The emulsifiable concentrate obtained according to Formulation of Formulation Example 2 was diluted with water so as to control the concentration of the compound to 125 ppm. The diluted solution was sprayed over a tomato leaf obtained by cutting and then air-dried. Using absorbent cotton, the leaf was fixed to a flask so that a front surface of the leaf faces upward. Seven pairs of adults of sweetpotato whitefly (type B) were inoculated in this container, and the container was placed in a temperature-controlled room at a temperature of 25° C. and a humidity of 65%. After 2 days, life and death were examined and the insecticidal rate was determined. The test was repeated twice.

In the present test, the following compounds showed the insecticidal rate of 100%.

Compound numbers 1-2, 1-3, 2-1, 2-2, 2-3, 2-4, 2-5, 2-6, 2-8, 2-9, 2-11, 2-12, 2-13, 2-14, 2-15, 2-16, 2-17, 2-18, 2-19, 2-20, 2-22, 2-24, 2-25, 2-26, 2-27, 2-29, 2-31, 2-33, 2-34, 2-35, 2-36, 2-37, 2-38, 2-39, 2-40, 2-41, 2-42, 2-44, 2-46, 2-47, 2-48, 2-49, 2-50, 2-51, 2-52, 2-53, 2-54, 2-55, 2-56, 2-57, 2-58, 2-59, 2-62, 2-63, 2-64, 2-65, 2-66, 2-67, 2-68, 2-70, 2-71, 2-72, 2-73, 2-74, 2-75, 2-76, 2-77, 2-78, 2-79, 2-80, 2-81, 2-83, 2-84, 2-85, 2-86, 2-87, 2-88, 2-89, 2-90, 2-91, 2-92, 2-93, 2-94, 2-95, 2-97, 2-98, 2-99, 2-100, 2-101, 2-102, 2-103, 2-104, 2-106, 2-109, 2-110, 2-112, 2-114, 2-115, 2-116, 2-117, 2-118, 2-119, 2-121, 2-122, 2-123, 2-124, 2-127, 2-128, 2-129, 2-130, 2-131, 2-132, 2-133, 2-148, 2-149, 2-150, 2-151, 4-3, 4-4, 6-1, 6-2, 6-5, 6-6, 6-7, 6-8, and 6-9.

Test Example 4

Confirmation and Efficacy Tests Against Twospotted Spider Mite (*Tetranychus Urticae* Koch)

The wettable powder obtained according to Formulation of Formulation Example 1 was diluted with water so as to control the concentration of the compound to 125 ppm. Seventeen female adults of twospotted spider mite with resistance to an organophosphorus agent were inoculated on a first true leaf of a kidney bean plant (approximately 7 to 10 days after sprouting) sown in a 3 sun/size pot (9 cm). The diluted solution was sprayed. The pot was placed in a temperature-controlled room at a temperature of 25° C. and a humidity of 65%. After 3 days, the adulticidal rate was examined. The test was repeated twice.

In the present test, the following compounds showed the adulticidal rate of 100%.

Compound numbers 2-2, 2-3, 2-4, 2-6, 2-11, 2-12, 2-13, 2-14, 2-15, 2-17, 2-20, 2-27, 2-34, 2-35, 2-36, 2-38, 2-40, 2-41, 2-46, 2-48, 2-49, 2-50, 2-51, 2-56, 2-59, 2-64, 2-68, 2-70, 2-71, 2-72, 2-73, 2-75, 2-76, 2-77, 2-78, 2-79, 2-80, 2-81, 2-83, 2-84, 2-85, 2-86, 2-87, 2-89, 2-90, 2-92, 2-94, 2-99, 2-100, 2-101, 2-102, 2-103, 2-104, 2-105, 2-106, 2-110, 2-111, 2-113, 2-114, 2-117, 2-118, 2-119, 2-124, 2-148, 2-149, 2-150, 2-151, 4-4, 6-1, 6-2, 6-6, and 6-7.

Test Example 5

Confirmation and Efficacy Tests Against Autogenic House Mosquito (*Culex Pipiens Molestus Forskal*)

In a 96-well microplate, five to ten larvae of autogenic house mosquitoes (1 day after hatching) and 0.225 ml of distilled water containing 0.5 mg of a diet for aquarium fish (Tetramin, manufactured by Tetra Japan & Spectrum Brands, Inc.) were charged. A 1% solution of the compound was prepared by using dimethyl sulfoxide (containing 0.5% of Tween 20) and then diluted to 0.01% with distilled water. This diluted chemical solution (0.025 ml) was stirred and added to the microplate including autogenic house mosquitoes therein (final concentration of the compound: 0.001%). The microplate was allowed to stand at a temperature of 25° C. After 2 days, the insecticidal rate was examined. The test was repeated twice.

In the present test, the following compounds showed the insecticidal rate of 90% or more and thus the compounds were effective.

Compound numbers 1-1, 1-2, 1-3, 2-1, 2-2, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 2-21, 2-22, 2-23, 2-24, 2-25, 2-26, 2-27, 2-28, 2-29, 2-30, 2-31, 2-33, 2-34, 2-35, 2-36, 2-37, 2-38, 2-39, 2-40, 2-41, 2-42, 2-43, 2-45, 2-46, 2-47, 2-48, 2-49, 2-50, 2-51, 2-52, 2-53, 2-54, 2-56, 2-57, 2-58, 2-59, 2-60, 2-61, 2-62, 2-63, 2-64, 2-65, 2-66, 2-67, 2-68, 2-69, 2-70, 2-71, 2-72, 2-73, 2-74, 2-75, 2-76, 2-77, 2-78, 2-79, 2-80, 2-81, 2-82, 2-83, 2-84, 2-85, 2-86, 2-87, 2-88, 2-89, 2-90, 2-91, 2-92, 2-93, 2-94, 2-95, 2-96, 2-97, 2-99, 2-100, 2-101, 2-102, 2-103, 2-104, 2-105, 2-106, 2-108, 2-109, 2-110, 2-111, 2-112, 2-113, 2-114, 2-115, 2-116, 2-117, 2-118, 2-119, 2-120, 2-121, 2-122, 2-123, 2-124, 2-125, 2-126, 2-127, 2-128, 2-130, 2-131, 2-132, 2-133, 2-148, 2-149, 2-150, 2-151, 4-1, 4-2, 4-3, 4-4, 4-5, 4-7, 6-1, 6-2, 6-3, 6-4, 6-5, 6-6, 6-7, 6-8, and 6-9.

Test Example 6-1

Confirmation and Efficacy Tests Against German Cockroach (*Blattella Germanica*)

The compound of the present invention was diluted with acetone to prepare a chemical solution having the concentration of 2,000 ppm. This chemical solution (250 μL) was added dropwise to 0.5 g of an artificial diet for rat, followed by air-drying. The artificial diet for rat treated with the chemical solution was put in a plastic container made of plastic and ten first instar larvae (in a state of mixing males and females) of german cockroaches were released and, after covering, the plastic container was housed in a temperature-controlled room at 25° C. After 5 days, the insecticidal rate (%) was determined.

In the present test, the following compounds showed the insecticidal rate of 80% or more and thus the compounds were effective.

Compound numbers 2-2, 2-6, 2-11, 2-16, 2-17, 2-18, 2-19, 2-20, 2-23, 2-26, 2-29, 2-33, 2-48, 2-51, 2-53, 2-54, 2-62, 2-63, 2-64, 2-66, 2-68, 2-75, 2-76, 2-78, 2-79, 2-80, 2-81, 2-83, 2-85, 2-86, 2-87, 2-91, and 2-93.

Test Example 6-2

Confirmation and Efficacy Tests Against German Cockroach (*Blattella Germanica*)

The compound of the present invention was diluted with DMSO to prepare a chemical solution having the concentration of 2,000 ppm. This chemical solution (10 µL), 500 µL of 10% sugar water and 500 µL of an aqueous 2% agar solution were mixed to prepare a jelly-like poison bait. The jelly-like poison bait was put in a plastic container and ten first instar larvae (in a state of mixing males and females) of german cockroaches were released and, after covering, the plastic container was housed in a temperature-controlled room at 25° C. After 5 days, the insecticidal rate (%) was determined.

In the present test, the following compounds showed the insecticidal rate of 80% or more and thus the compounds were effective.

Compound numbers 2-11, 2-39, 2-40, 2-41, 2-46, 2-51, and 6-1.

Test Example 7

Confirmation and Efficacy Tests Against House Fly (*Musca Domestica*)

A 5% emulsifiable concentrate of the compound of the present invention was diluted with 10% sugar water to prepare a chemical solution having the concentration of 125 ppm. Absorbent cotton impregnated with 8 mL of the chemical solution was put in a plastic container and ten female adults of house flies were released and, after covering, the plastic container was housed in a temperature-controlled room at 25° C. After 3 days, the insecticidal rate (%) was determined.

In the present test, the following compounds showed the insecticidal rate of 80% or more and thus the compounds were effective.

Compound numbers 2-2, 2-6, 2-11, 2-16, 2-17, 2-18, 2-19, 2-20, 2-23, 2-26, 2-29, 2-33, 2-39, 2-40, 2-41, 2-42, 2-46, 2-48, 2-51, 2-53, 2-54, 2-62, 2-63, 2-64, 2-66, 2-68, 2-75, 2-76, 2-78, 2-79, 2-80, 2-81, 2-83, 2-85, 2-86, 2-87, 2-91, 2-93, and 6-1.

Test Example 8

Confirmation and Efficacy Tests Against Scrub Tick (*Haemaphysalis Longicornis*)

The compound of the present invention was diluted with acetone to prepare a chemical solution having the concentration of 400 ppm. After applying 118 µL of the chemical solution to an inner surface of a 20 mL volume glass vial, acetone was vaporized to form a thin film of the compound of the present invention on the inner surface of the glass vial. Since the glass vial used has the inner surface of 47 cm², the treating amount of a chemical is 1 µg/cm². Ten larvae of scrub ticks were put in the glass vial and, after covering, the plastic container was housed in a temperature-controlled room at 25° C. After 5 days, the insecticidal rate (%) was determined.

In the present test, the following compounds showed the insecticidal rate of 80% or more and thus the compounds were effective.

Compound numbers 2-2, 2-6, 2-11, 2-51, 2-68, 2-76, 2-78, 2-79, 2-81, and 2-85.

Test Example 9

Confirmation and Efficacy Tests Against Cat Flea (*Ctenocephalides felis*)

The compound of the present invention was diluted with acetone to prepare a chemical solution having the concentration of 40 ppm. After applying 118 µL of the chemical solution to an inner surface of a 20 mL volume glass vial, acetone was vaporized to form a thin film of the compound of the present invention on the inner surface of the glass vial. Since the glass vial used has the inner surface of 47 cm², the treating amount of a chemical is 0.1 µg/cm². Five larvae of cat flea were put in the glass vial and, after covering, the plastic container was housed in a temperature-controlled room at 25° C. After 2 days, the insecticidal rate (%) was determined.

In the present test, the following compounds showed the insecticidal rate of 80% or more and thus the compounds were effective.

Compound numbers 2-2, 2-6, 2-11, 2-51, 2-68, 2-76, 2-78, 2-79, 2-81, and 2-85.

INDUSTRIAL APPLICABILITY

According to the present invention, it is possible to provide a 1-heterodiene derivative having a novel structure or a salt thereof. The present invention can also provide a pest control agent including, as an active ingredient, the 1-heterodiene derivative or a salt thereof, which has excellent biological activity, particularly excellent biological activity against insects and acarids, and also has high safety.

The invention claimed is:

1. A 1-heterodiene derivative represented by Formula (1):

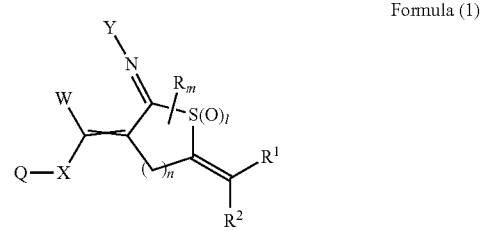

Formula (1)

wherein Q in Formula (1) represents a non-substituted or substituted C1-6 alkyl group, a non-substituted or substituted C2-6 alkenyl group, a non-substituted or substituted C2-6 alkynyl group, a non-substituted or substituted C3-8 cycloalkyl group, a non-substituted or substituted C4-8 cycloalkenyl group, a non-substituted or substituted C6-10 aryl group, or a non-substituted or substituted heterocyclic group;

W represents a hydrogen atom, or a non-substituted or substituted C1-6 alkyl group;

Y represents a non-substituted or substituted C6-10 aryl group, a non-substituted or substituted C3-8 cycloalkyl group, or a non-substituted or substituted heterocyclic group;

X represents an oxygen atom, a sulfur atom, a sulfinyl group, or a sulfonyl group;

l represents the number of oxygen atoms in parenthesis and is any one integer of 0 to 2;

n represents the repeat number of methylene groups in parenthesis and is any one integer of 1 to 4;

R represents a non-substituted or substituted C1-6 alkyl group, a non-substituted or substituted C2-6 alkenyl group, a non-substituted or substituted C2-6 alkynyl group, a non-substituted or substituted C3-8 cycloalkyl group, a non-substituted or substituted C4-8 cycloalkenyl group, a non-substituted or substituted C6-10 aryl group, or a non-substituted or substituted heterocyclic group;

m represents the number of R(s) and is any one integer of 0 to 8 and, when m is 2 or more, R may be the same or different, and also any plural R(s) may be combined to form a non-substituted or substituted 3- to 8-membered ring; and $R^1$ and $R^2$ each independently represents a hydrogen atom, a non-substituted or substituted C1-6 alkyl group, or a non-substituted or substituted C3-8 cycloalkyl group, and $R^1$ and $R^2$ may be combined to form a non-substituted or substituted 3- to 8-membered ring;

or a salt thereof.

2. The 1-heterodiene derivative according to claim 1, wherein n is 2, or a salt thereof.

3. The 1-heterodiene derivative according to claim 1, wherein Q is a non-substituted or substituted C6-10 aryl group, or a non-substituted or substituted heterocyclic group, or a salt thereof.

4. The 1-heterodiene derivative according to claim 1, wherein Y is a non-substituted or substituted C6-10 aryl group, or a salt thereof.

5. A pest control agent comprising, as an active ingredient, at least one selected from the 1-heterodiene derivative according to claim 1 and a salt thereof.

6. The pest control agent according to claim 5, wherein the pest is an insect or acarid.

* * * * *